United States Patent [19]
Bramble et al.

[11] Patent Number: 6,096,544
[45] Date of Patent: Aug. 1, 2000

[54] METHOD OF IMPROVED MIXING IN ROLLER BOTTLES

[75] Inventors: Joye L. Bramble, Lansdale, Pa.;
Fernando J. Muzzio, Spotswood, N.J.;
James A. Searles, Boulder, Colo.

[73] Assignees: Merck & Co., Inc., Rahway; Rutgers, The State University of New Jersey, New Brunswick, both of N.J.

[21] Appl. No.: 09/178,974

[22] Filed: Oct. 26, 1998

Related U.S. Application Data

[60] Provisional application No. 60/063,854, Oct. 31, 1997, and provisional application No. 60/067,371, Dec. 3, 1997.

[51] Int. Cl.$^7$ ........................................................ C12M 3/02
[52] U.S. Cl. .................... 435/394; 435/395; 435/286.7; 435/303.3; 435/304.1; 366/219
[58] Field of Search ............................... 435/3, 394, 403, 435/395, 286.7, 298.2, 303.3, 304.1; 366/208, 219

[56] References Cited

U.S. PATENT DOCUMENTS

| | | |
|---|---|---|
| 3,091,435 | 5/1963 | Pease . |
| 3,682,080 | 8/1972 | Merz . |
| 3,705,544 | 12/1972 | Ratowsky . |
| 3,981,488 | 9/1976 | Ratowsky . |
| 3,982,259 | 9/1976 | Van Baerle . |
| 4,373,029 | 2/1983 | Nees . |
| 5,153,133 | 10/1992 | Schwarz et al. . |

OTHER PUBLICATIONS

J.R. Archer, International PDA Meeting, pp. 17–21, (Feb. 1991).
J.H. Hughes, Clinical Microbiology Reviews, vol. 6(2), pp. 150–175 (Apr. 1993).
R.M. Gallegos Gallegos, et al., Archives of Medical Research, vol. 26(1), pp. 59–63, (1995).
J.H. Hughes, et al., Journal of Virological Methods, vol. 22 pp. 75–80 (1988).
V.G. Edy, Adv. Exp. Med. Biol., vol. 172, pp. 169–178, (1984).
H. Kotani, et al., Human Gene Therapy, vol. 5, pp. 19–28, (1994).
R. Kunitake, et al., Journal of Biotechnology, vol. 52, pp. 289–294, (1997).
B.J. Montagnon, Tropical and Geographical Medicine, vol. 37(3), pp. S40–41, (Sep. 1985).
E. Rivera, et al., Research Veterinary Science, vol. 41, pp. 391–396, (Nov. 1986).
A.Y. Elliott, "Nonpurfused Attachment Systems for Cell Cultivation", pp. 207–216 (A.S. Lubiniecki, Ed, "Large Scale Mammalian Cell Culture Technology", Marcel Dekker (1990)).
J.L. Melnick, et al., Prop. Soc. Exp. Biol. Med., vol. 81, pp. 208–213, (1952).
E.I. Tsao, et al., Annals NY Acad. of Science, vol. 665, pp. 127–136, (1992).
G.A. Zimmermann, et al., Journal of Immunology, vol. 134(3), pp. 1866–1874, (Mar. 1985).
J. Novotny, et al., Acta Virol., vol. 36, pp. 483–487, (1992).
W.R. Earle, et al., Annals NY Acad. of Science, vol. 58, pp. 1000–1011, (1954).
M.A. Sturgill, et al., Journal of Clinical Microbiology, vol. 27(3), pp. 577–579, (1989).

*Primary Examiner*—David A. Redding
*Attorney, Agent, or Firm*—Valerie J. Camara; Mark R. Daniel

[57] ABSTRACT

A method for enhancing the mixing of materials in a roller bottle by the introduction of controlled axial and cross-sectional flow perturbations is disclosed. The effectiveness of the method is demonstrated by achieving higher efficiency in cell culturing and virus propagation in roller bottles by introducing controlled flow perturbations during the process.

29 Claims, 29 Drawing Sheets

(15 of 29 Drawing Sheet(s) Filed in Color)

METHOD OF IMPROVED MIXING IN ROLLER BOTTLES

This application claims benefit of provisional application Ser. No. 60/063,854 filed Oct. 31, 1997, and a provision of Ser. No. 60/067,371 filed Dec. 3, 1997.

BACKGROUND OF THE INVENTION

Manual and automated roller bottle systems have been used for over 40 years in the pharmaceutical, biochemical, and medical fields for processes such as cell growth and infection, heterologous glycoprotein production, vaccine preparation, and high density plant cell cultivation. [H. Tanaka, F. Nishijima, M. Suwa, and T. Iwamoto, *Biotechnol. Bioeng.* 25, 2359 (1983); H. Tanaka, *Process Biochem.* Aug., 106 (1987); C. Y. Hong, T. P. Labuza, and S. K. Harlander, *Biotechnol. Prog.* 5:4, 137 (1989); Y. A. Elliot, *Bioprocess Tech.* 10, 207 (1990); V. G. Kalthod, *Novel Carrier and Reactor for Culture of Attachment Dependent Mammalian Cells.* D. SC. Thesis. Washington University, St. Louis, Mo. (1991); E. I. Tsao, M. A. Bohn, D. R. Omstead, and M. J. Munster. *Annals N.Y. Acad. Sci.* 665, 127 (1992); R. Pennell and C. Milstein, *J. of Immun. Meth.* 146, 43 (1992); E. Olivas, B. B. D.-M. Chen, and W. S. Walker, *J. Immun. Meth.* 182, 73 (1995); R. Singhvi, J. F. Markusen, B. Ky, B. J. Horvath, and J. G. Aunins, *Cytotechnology* 22, 79 (1996); R. Kunitake, A. Suzuki, H. Ichihashi, S. Matsuda, O. Hirai, and K. Morimoto, *J. Biotechnology* 52:3, 289 (1997).]. Despite efforts by numerous investigators to develop unit operation based systems, such as microcarrier cultures, for the production of anchorage dependent cells or cell products [E. Van Hemert, D. G. Kilburn, and A. L. Van Wezel, *Biotechnol. Bioeng.* 11, 875 (1969); C. Horng and W. McLimans, *Biotechnol. Bioeng.* 17, 713 (1975); R. E. Spier and J. P. Whiteside, *Biotechnol. Bioeng.* 18, 649 (1976); D. W. Levine, D. Wang, and W. G. Thilly, *Biotechnol. Bioeng.* 2, 821 (1979); J. J. Clark and M. D. Hirtenstein, *J. Interferon Research* 1, 391 (1981); B. J. Montagnon, B. Fanget, and A. J. Nicolas, *Developments in Biological Standards* 47, 55 (1981); V. G. Edy, *Adv. Exp. Med. Biol.* 172, 169 (1984); E. Rivera, C. G. Sjosten, R. Bergman, K. A. Karlsson, *Research in Veterinary Science* 41, 391 (1986); and R. M. Gallegos Gallegos, E. L. Espinosa Larios, L. R. Ramirez, R. K. Schmid, and A. G. Setien, *Archives in Medical Research* 26:1, 59 (1995).], roller bottle systems still prevail in research and industry. Additionally, for industrial scale production of cell culture products (i.e. vaccines), cells are frequently passaged in roller bottles prior to transfer to microcarrier cultures for the final growth phase even when unit operation based systems are utilized [V. G. Edy, *Adv. Exp. Med. Biol.* 172, 169 (1984)].

Widespread use of the roller bottle is due to several reasons. Most notably, the process relies on very simple technology: a horizontal cylindrical vessel is filled approximately one-third full and axially rotated. Thus, scale-up development is not required, resulting in reduced developmental timelines for industry and faster introduction to market for new products. The system allows constant fluid-gas contact, and easy addition of nutrients without interruption of the process. In addition, the process is capable of maintaining sterile conditions for prolonged times, contamination of one or more roller bottles does not result in the contamination of an entire lot, precise control of nutrient and waste-product levels is possible, and the direct monitoring of the cells is relatively simple [E. I. Tsao, M. A. Bohn, D. R. Omstead, and M. J. Munster. *Annals N.Y. Acad. Sci.* 665, 127 (1992)].

On the other hand, roller bottles are limited in surface area available for growth and in the volume of harvest fluid obtained. Manpower and facility space requirements are higher than for unit operation systems such as microcarriers, since hundreds of roller bottles are typically operated for a single production run; although, new automation systems are addressing this issue [R. Kunitake, A. Suzuki, H. Ichihashi, S. Matsuda, O. Hirai, and K. Morimoto, *J. Biotechnology* 52:3, 289 (1997); and R. Archer and L. Wood, Proceedings of the 11th Annual Meeting of European Society for Animal Cell Technology, Brighton, U.K., Sep. 2–6, 1991.]. In addition, the performance of cell growth and infection is believed to be significantly reduced due to flow end mixing dynamics, perhaps by preventing infected cells from attaching to host cells attached to the bottle walls [Y. A. Elliot, *Bioprocess Tech.* 10, 207 (1990)]. Although these issues point toward an obvious need for flow analysis and process design criteria, there have been no published results to date on either of these topics.

The conventional method of mixing in roller bottles is inefficient. The bottles are generally rotated at a uniform rate in one direction for cell planting, cell growth and/or virus propagation. A rotation frequency of 0.125 rpm to 5.0 rpm is typical. This uniform rotation, however, results in the formation of dead zones within the roller bottle where cells or other particles such as viruses are trapped in cyclic orbits, never making it to the surface of the roller bottle. At cell planting, for anchorage-dependent cells, it is important that the cells come in contact rapidly with the sides of the roller bottle, since only then can the cells become attached to the container wall and form the cell sheets. Slow attachment leads to low viability of the cells and/or inhomogeneous planting, and hence inhomogeneous growth on the roller bottle surface. During cell growth, such inefficient mixing limits cell growth because the poorly mixed medium does not supply the cells with adequate nutrients (e.g. oxygen) or remove toxins (e.g. carbon dioxide) from a submerged, surface-attached cell sheet as the bottle rotates. During propagation of many viruses, the rapidity of virus attachment to the cells is important to maintain inoculum infectivity and to achieve a rapid and homogeneous infection. Again, poor liquid mixing thwarts these goals.

The shortcomings of conventional roller bottle mixing are underscored when it is applied to virus propagation, especially for viruses where the virus inoculum to the process is an infected cell suspension. This is the case for several herpesviruses such as Marek's Disease Virus of poultry (D. Ben Nathan and S. Lustig "Production of Marek's Disease Vaccine" in Viral Vaccines, Wiley-Liss, 1990, pp. 347–365), and *Varicella Zoster* Virus (P. J. Provost et al. U.S. Pat. Nos. 5,360,736 and 5,607,852; and Krah et al. "Enhancement of *Varicella-zoster* Virus Plaquing Efficiency with an Agrarose Overlay Medium" J. Vir. Methods 27, pp.319–326 (1990).). The efficiency of virus propagation is dependent on the infectious cells coming in contact with the cell sheet, where infectious foci are created. The infection then spreads across the cell sheet from these foci. In conventional roller bottle mixing, however, many infectious cells become trapped in closed, symmetrical orbits and never reach the cell sheet on the bottle surface. In addition, conventional roller bottles display poor axial mixing, resulting in large heterogeneous areas.

The instant application describes detail mathematical and experimental characterizations of the fluid flow profiles within rotating roller bottles, including particle trajectories, fluid mixing patterns, and unsteady-state flow strategies. The results point to ways in which cell proliferation and infection can be optimized by simple modifications to the roller bottle's rotation. Thus, the instant invention describes an improved method for mixing in roller bottles that introduces cross-sectional and axial flow perturbations. These perturbations disrupt the closed orbits that cells experience during conventional mixing and facilitate particle settling. Furthermore, this invention relates to a mixing process that ensures that cells come in contact with adequate amounts of nutrient-rich medium and by increasing the contact between the cells and the roller bottle wall or cell sheet and thereby enhances productivity.

SUMMARY OF THE INVENTION

This invention relates to a method for enhanced mixing in a roller bottle by the introduction of controlled axial and cross-sectional flow perturbations. The effectiveness of the method is demonstrated by achieving higher efficiency in cell culturing and virus propagation in roller bottles.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

(a) Schematic diagram of the roller bottle. (b) Schematic diagram of the computational grid used for the simulations.

FIG. 2.

(a) Particle imaging velocimetry determination of the velocity field at the center plane of the bottle. (b) Finite element results. Velocity field at the center plane of the bottle.

FIG. 3.

Computational streamlines of the flow at the center plane of the bottle under steady flow conditions.

FIGS. 4a–e.

Figure 4A:
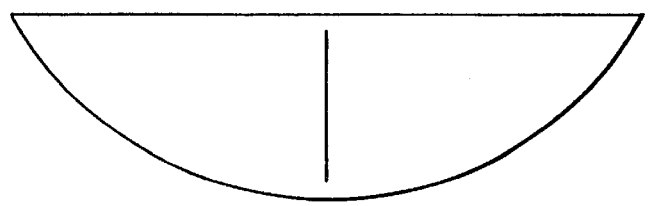
Figure 4B:
Figure 4C:
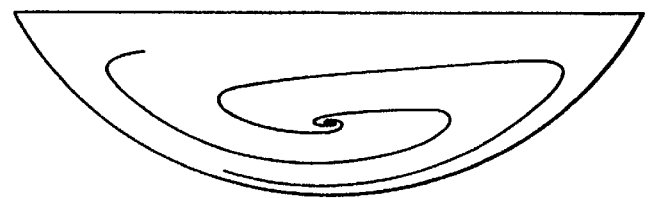
Figure 4D:
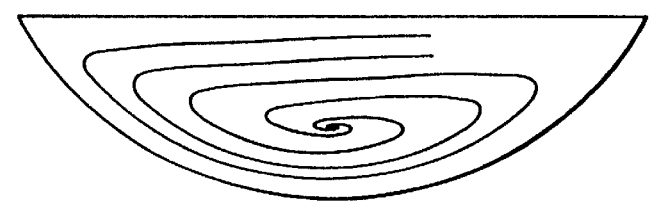
Figure 4E:
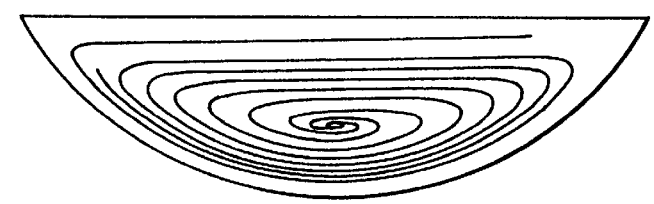

Evolution of a vertical line placed in the flow field. FIG. 4a shows the initial condition and FIGS. 4b through 4e represent the initial condition and the line after 4, 8, 16, and 32 bottle revolutions, respectively.

FIG. 5.

Initial condition for the flow visualization experiment. The fluorescent dye was placed in the center of the bottle axially so that end effects would cancel.

FIG. 6.

Experimental validation of the evolution of a vertical line place in the flow field.

FIGS. 7A–F.

Finite element results. Velocity field at several vertical planes spaced along the axis of the bottle.

FIG. 8.

Finite element results. Velocity field at a horizontal plane near the upper surface of the fluid.

FIG. 9.

Pathlines of passive tracer particles starting from different positions inside the bottle.

FIG. 10.

Path lines of six particles with settling velocity of $V_s=0.05U$ placed in the flow.

FIG. 11.

Experimental validation of a particle pathline in the flow; the particle had a settling velocity of approximately 0.06 U.

FIG. 12.

Final positions of particles, initially distributed uniformly in the central vertical cross-section of the bottle, for settling velocities of $V_s=0$, 0.02U, 0.05U, 0.1U and 0.2 U, respectively.

FIGS. 13A–13D.

Contour plots of residence time of particles against the particles initial position for (a) $V_s=0.02U$, (b) 0.05U, (c) 0.1U, and (d) 0.2U after 20 bottle revolutions. The colors in this figure range from dark blue to red, and correspond to zero residence time to infinite residence time.

FIG. 14.

Number of particles suspended in the flow as a function of time for a variety of settling velocities.

FIG. 15.

Fraction of cells remaining in the supernatant as a function of roller bottle rotation rate.

FIG. 16.

Relative quantity of infectious foci on the cell monolayer as a function of rotation rate.

FIG. 17.

Relative quantity of infectious foci on the cell monolayer as a function of rotation rate, for lower rotation rates.

FIG. 18.

Cell growth rates and final cell densities as a function of rotation rate.

FIG. 19.

Number of particles suspended in the flow as a function of time for a variety of period lengths. The settling velocity for all figures was the same, $V_s=0.003U$.

FIGS. 20A; 20B.

Experimental apparatus used to investigate mixing enhancement via introduction of rocking motion.

FIGS. 21a–21i.

Figure 21A:
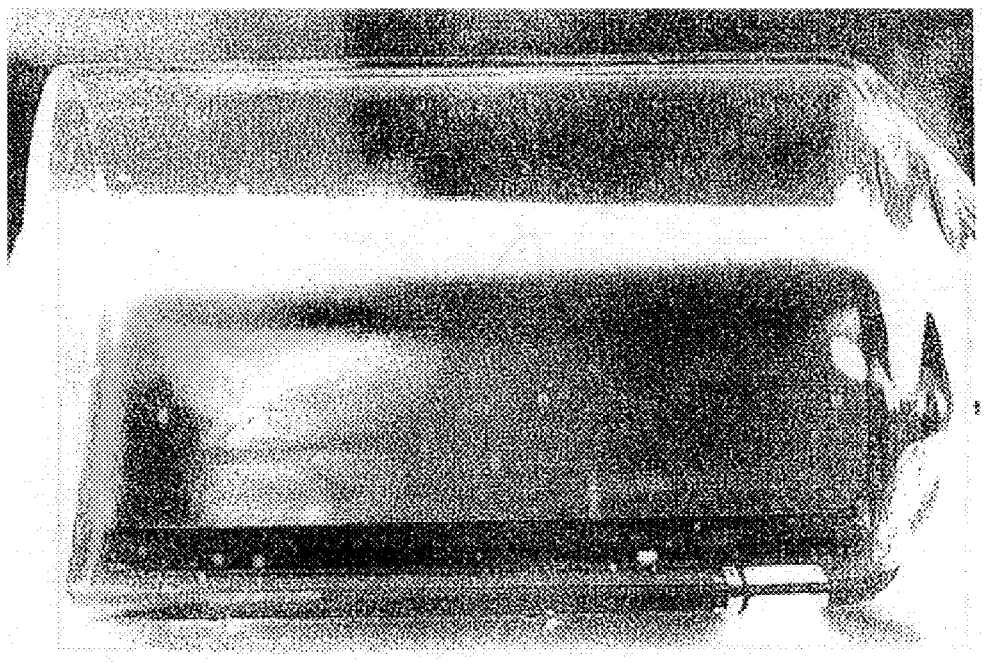
Figure 21B:
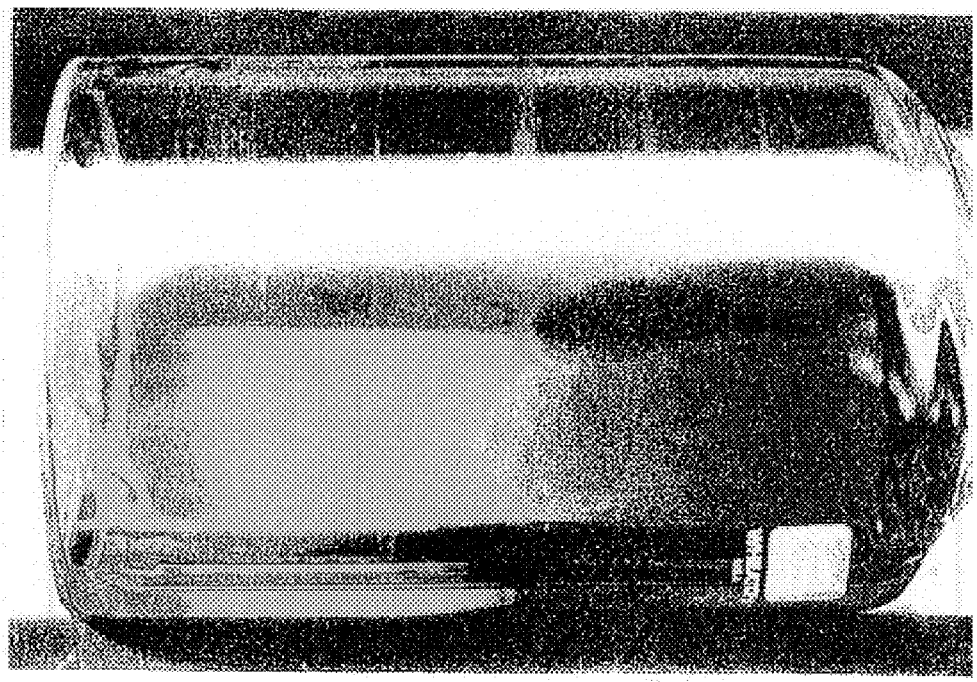
Figure 21C:
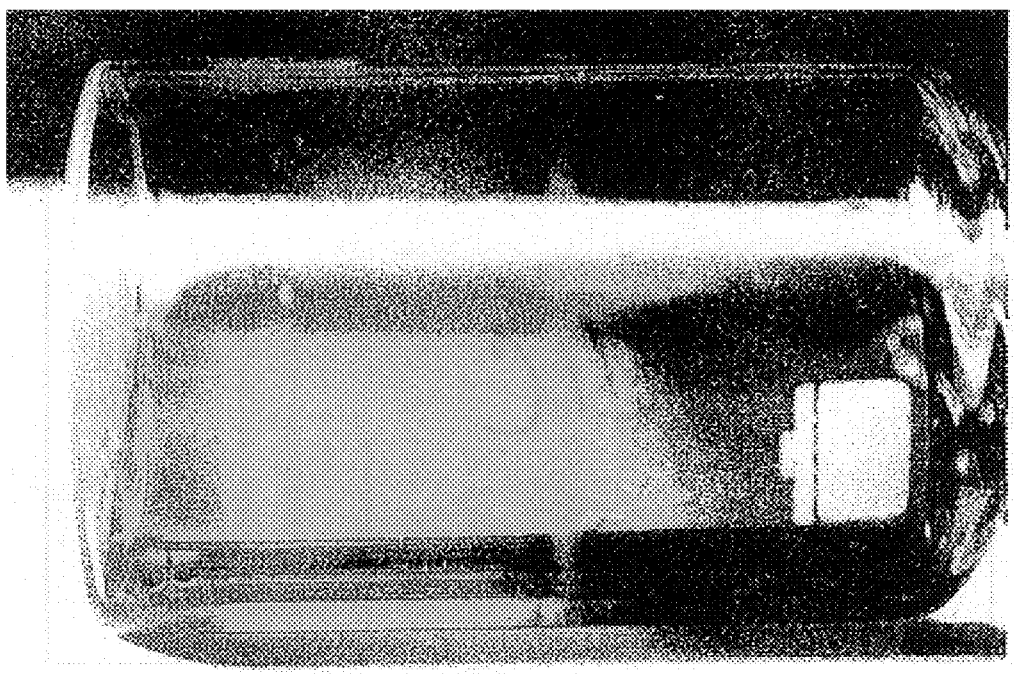
Figure 21D:
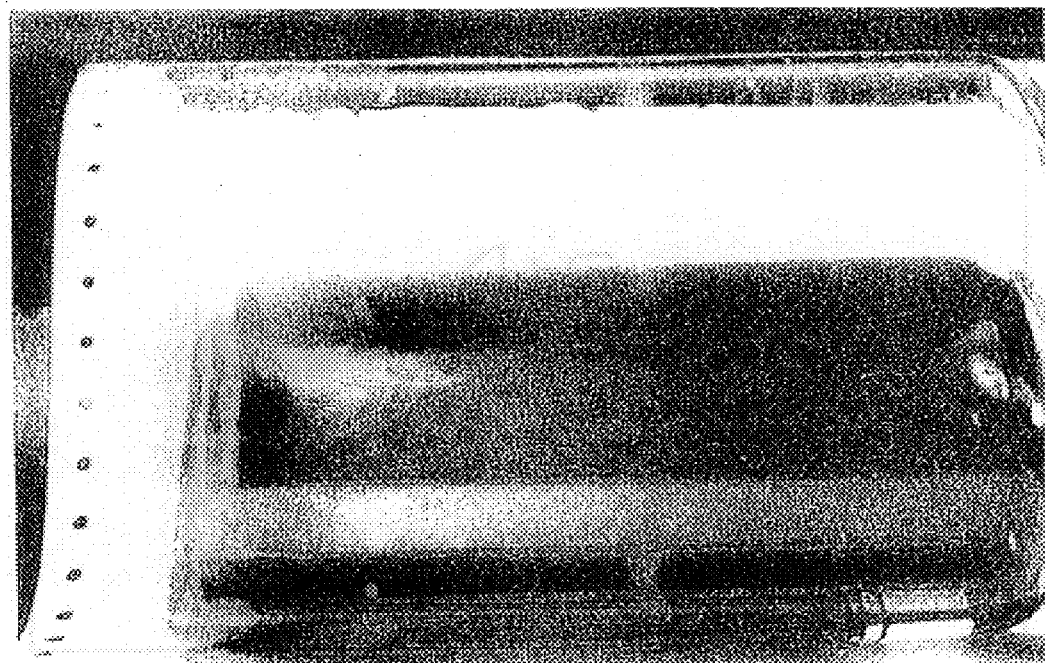
Figure 21E:
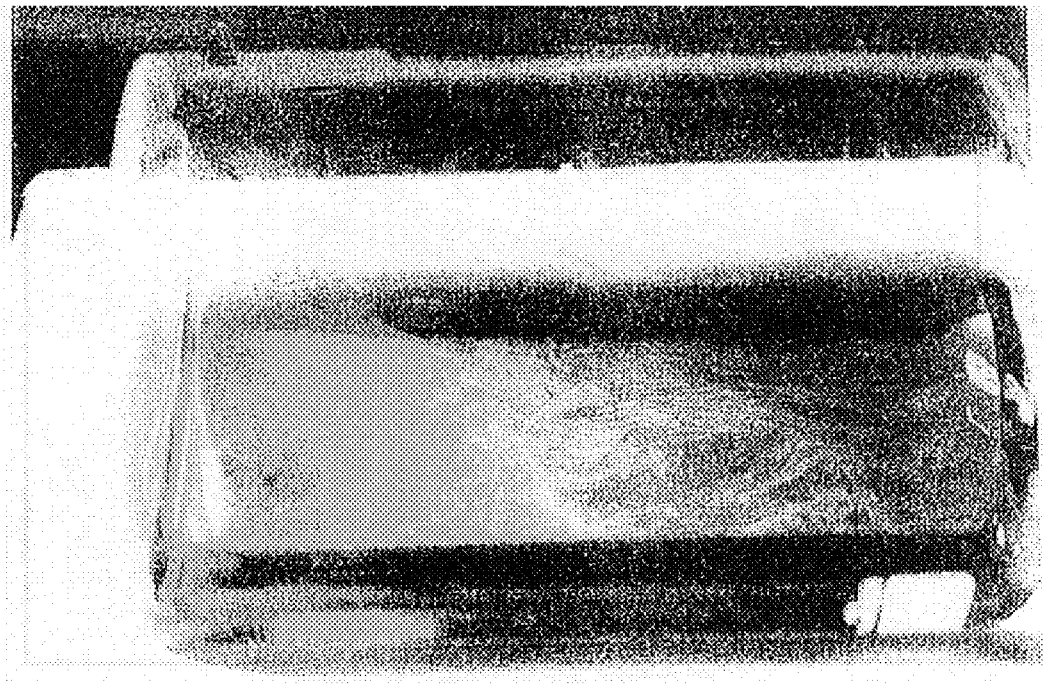
Figure 21F:
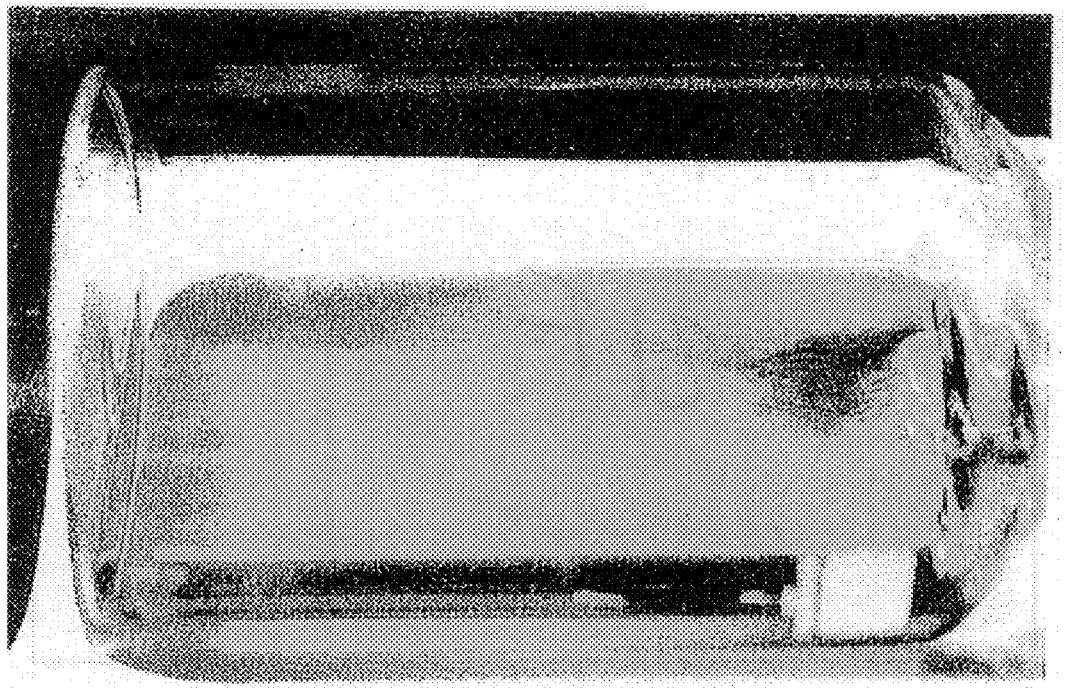
Figure 21G:
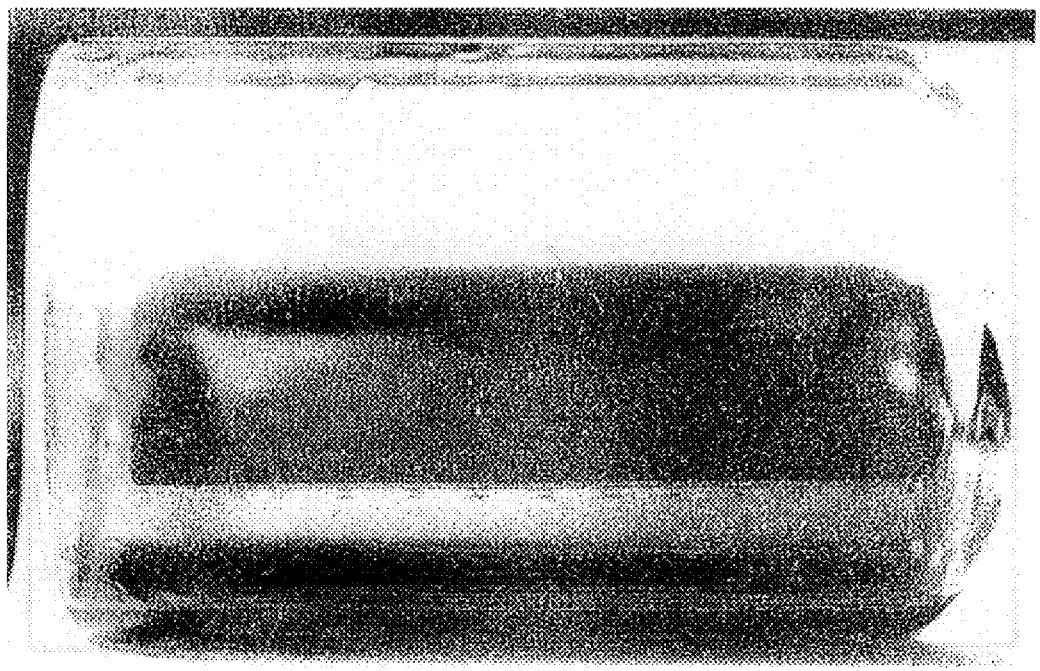
Figure 21H:
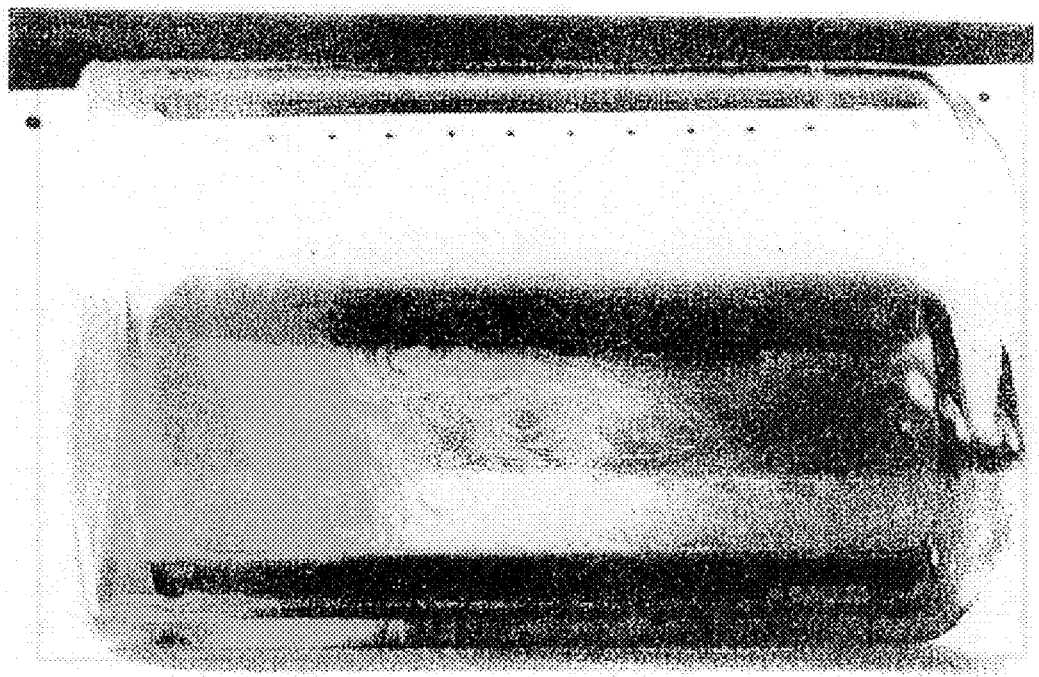
Figure 21I:
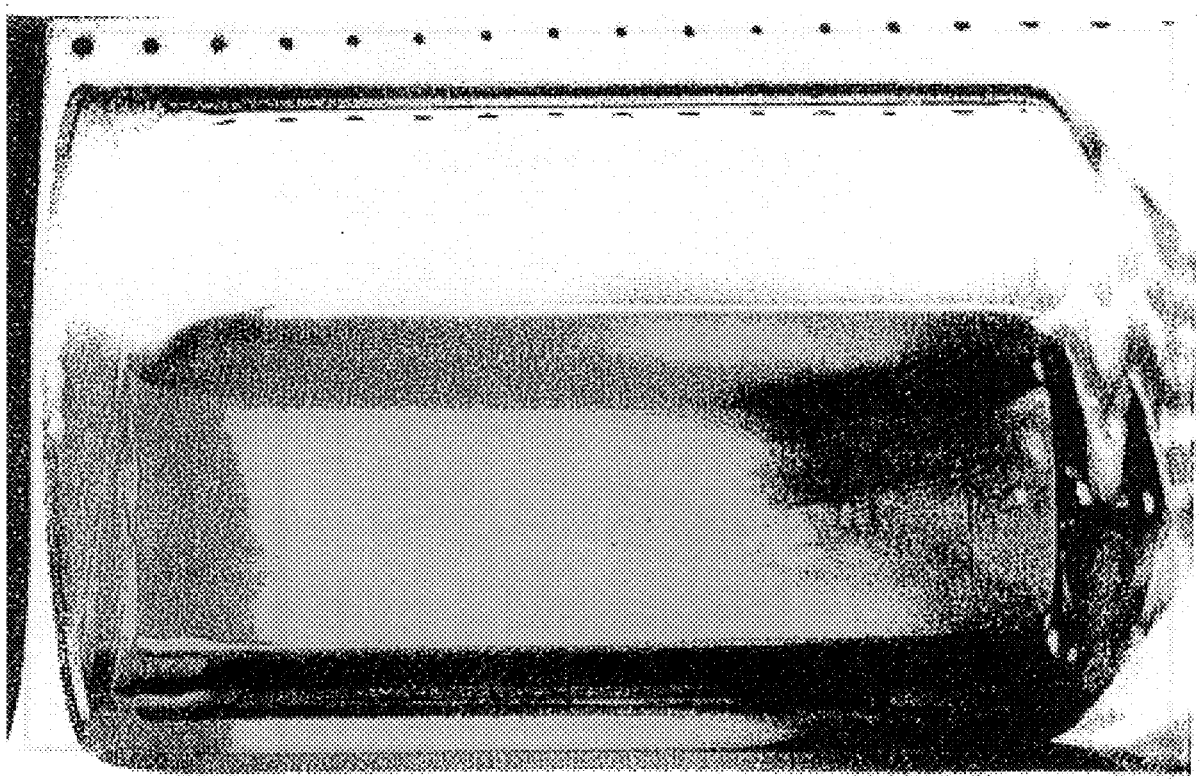

The effects of rocking on axial mixing. FIGS. 21(a)–21(c) demonstrate axial mixing with no rocking after 0, 32 and 64 revolutions, respectively. FIGS. 21(d)–21(f) demonstrate mixing with 12.047° rock and rotation of 1.6 revolutions per rock after 0, 32 and 64 revolutions, respectively. FIGS. 21(g)–21(i) demonstrate mixing with 12.047° rock and rotation of 3.2 revolutions per rock after 0, 32 and 64 revolutions, respectively.

FIG. 22.

Roller machine capable of introducing a rocking motion.

FIG. 23.

Protuberances on (a) the roller bottle and (b) rollers which introduce a rocking motion.

DETAILED DESCRIPTION OF THE INVENTION

The invention relates to a method for enhancing the mixing of materials in a roller bottle comprising controlled axial and cross-sectional flow perturbations.

An embodiment of this method is where the controlled flow perturbation is selected from the following group:

(a) uniform rotation of the roller bottle with a rocking motion, (b) time-dependent rotation speed of the roller bottle, (c) time-dependent rotation speed of the roller bottle with a rocking motion, (d) time-dependent rotation direction of the roller bottle, (e) time-dependent rotation direction of the roller bottle with a rocking motion, or (f) time-dependent rotation speed of the roller bottle combined with time-dependent rotation direction and a rocking motion.

The term "materials" refers to the a solution of or suspension of liquid and solid materials, such as a cell culture and the media needed to sustain that culture, the virus infected cells and the media needed to sustain these cells.

Uniform Rotation Of The Roller Bottle With A Rocking Motion

A mode of enhancing mixing and settling is to use a combination of rotation and rocking. The axis of rotation of the roller bottle is the axis defined by the line connecting the center of the roller bottle and running the length of the roller bottle. The rocking motion is defined as the angle swept by the roller bottle about an axis that is perpendicular to the axis of rotation of the roller bottle, that angle of about 0 degrees to about +20 degrees or −20 degrees, a speed of rotation of about 0 to about 50 rpm, and a rock to roll frequency of about 0 to about 31.4. The preferred conditions for the combined rotation of the bottle with rocking motion are defined by a rocking angle of about +10 degrees to about −10 degrees, and a rock to roll frequency of about 1.8.

Since rocking renders the flow geometry time-dependent, necessarily perturbing cell motion patterns, it is likely that this approach has the greatest impact. A computational approach to this problem would be very involved. Fortunately, the approach could be readily explored experimentally. Rocking enhances mixing in the roller bottle very significantly. This is demonstrated in FIGS. 5 and 6 by studying the mixing of glycerin and a pH indicator (Bromothymol Blue). Initially, the glycerin was mixed with the indicator and with 0.5 mL 1 M NaOH. This caused the glycerin to turn deep blue. With the roller bottle on the apparatus, approximately 20 mL of glycerin was then removed from the bottle with a syringe and mixed with 1.0 mL of 1 M HCl, turning the fluid yellow. This fluid was then injected back into the roller bottle near the back wall and mixed with the fluid at the base of the bottle with a specially modified spatula. The roller bottle was subsequently rolled. In experiments with real cells, the choice of rocking frequency would be restricted by considerations of keeping the cells submerged in the nutrient medium as uniformly as possible.

FIGS. 21 (a)–(c) shows the control experiment where there is no rocking. FIGS. 21 (d)–(i) shows two different rocking frequencies, 1.6 and 3.2 revolutions per rocking cycle. Without rocking, half of the bottle appears yellow after 32 revolutions, and after 64 revolutions the blue yellow interface has barely moved. On the other hand, when rocking is implemented, after 64 revolutions the fluid is completely yellow for both rocking frequencies, indicating that complete mixing has been achieved throughout the system. These results demonstrate that rocking indeed enhances mixing by disrupting cyclical cell motion and enhancing cell settling.

Figure 22:
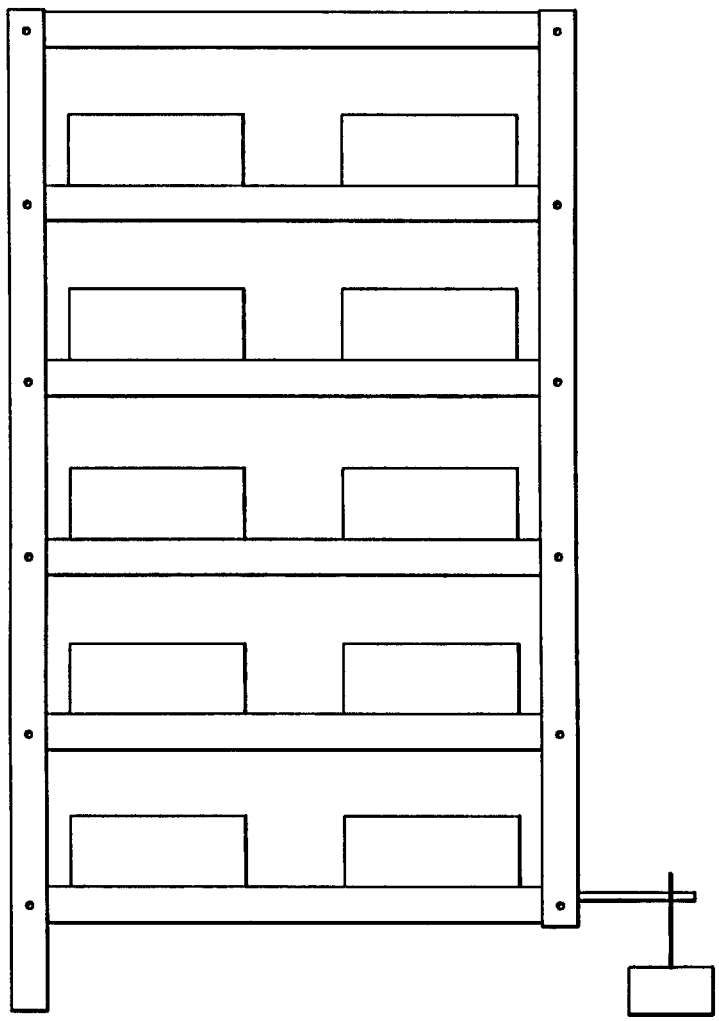
Figure 23A:
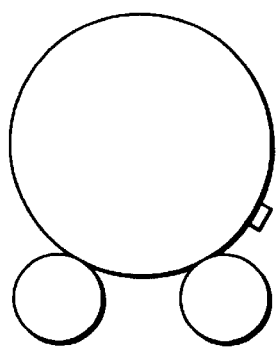
Figure 23B:
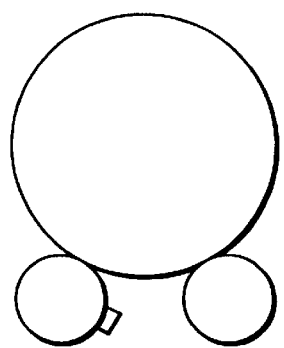

The rocking motion can be introduced in a number of ways, including but not limited to, introducing a rocking motion to a roller machine (FIG. 22), or by introducing protuberances to the rollers or the roller bottles (FIG. 23). The roller machine rack as depicted in FIG. 22, provides the most flexibility in varying the rock to roll frequency, rocking angle, frequency of bottle rotation and the speed of rotation. Additionally, a single level roller machine is also contemplated by the instant invention.

Time-Dependent Rotation Speed Of The Roller Bottle

Another way of disturbing periodic cell trajectories is to operate the bottle in a stop-go mode. The bottle motion consists of two alternating parts. The bottle is rotated at constant velocity U for a time $t_1$, and then it is kept stationary for a time $t_2$. During the second part of the flow period, cells undergo settling at terminal speed. The purpose of using this mode is to try to break the periodic cell orbit and let cells settle. Once again, preliminary results indicated that this mode of motion enhances settling, but the extent of the enhancement depends strongly on settling velocity.

Another approach is to vary the speed of rotation as a function of time. This approach has been applied to the varicella vaccine production process. Previously, the method had utilized a rotation rate of 0.25 rpm throughout. Experiments were conducted with faster rotation rates for the cell expansion phase and slower rotation rates for the first 6 hours of the infection phase. As described below, slower rotation rates during the virus propagation phase enabled more varicella-infected cells to reach the inside surfaces of the roller bottle sooner, resulting in higher levels of virus production. In addition, rotation faster than 0.25 rpm during the cell expansion phase resulted in more efficient cell growth.

Previous experiments demonstrated that the growth of anchorage dependent cells and cell culture products (i.e. varicella) in roller bottles were much less efficient than that observed in stationary cultures such as T-flasks. It was hypothesized that these differences were in part due to decreased cell (uninfected and infected cells) sedimentation rates present in the roller bottle cultures due to circulating liquid flows which trapped the particles in circular orbits. The decreased sedimentation times resulted in lower cell plating efficiencies for uninfected cells and increased degradation times for virus infected cells which were unable to reach the cell culture surface for attachment and/or infection.

The kinetics of virus infected cell sedimentation and attachment were studied at different rotation rates. Additionally, the attachment and growth of cells to the roller bottle surface were also studied to determine the primary mechanism controlling the differences observed in cell growth rates as a function of rotation rate.

Time-Dependent Rotation Speed Of The Roller Bottle With A Rocking Motion

The method for enhancing the mixing in a roller bottle, wherein the controlled axial flow perturbation is introduced by combining a time-dependent rotation speed of the roller bottle with a rocking motion, which is further defined by a speed of rotation of about 0 to about 50 rpm, a frequency of rotation rate changes per revolution of about 0 to about 1, a rocking angle of about 0° to about +10 degrees or −10 degrees, and a rock to roll frequency of about 0 to about 31.4.

Time-Dependent Rotation Direction Of The Roller Bottle

The first was to rotate the bottle back and forth. Intuitively, it was expected that particles would continue to fall through the fluid when the flow changed direction. Numerical results using the preliminary, two-dimensional flow model indeed confirmed this expectation, but settling enhancements showed significant variability depending on settling velocity.

Although it was not calculated in this case, it is possible to estimate the cell settling velocity experimentally. Cell settling in a stationary container could be directly observed using a stereoscope with a 100× magnification, connected to a videocamera and a VCR. Settling velocity could then be assessed by slowly playing the recorded cell motions as they settle through the field of view.

Time-Dependent Rotation Direction Of The Roller Bottle With A Rocking Motion The method for mixing in a roller bottle, wherein the controlled axial flow perturbation is introduced by combining a time-dependent rotation direction of the roller bottle with a rocking motion, which is further defined by a speed of rotation (roll frequency) of about 0 to about 50 rpm, and a frequency of rotation direction changes per revolution of about 0 to about 1, a rocking angle of about 0° to about +10 degrees or −10 degrees, and a rock to roll frequency of about 0 to about 31.4.

Time-Dependent Rotation Speed Of The Roller Bottle Combined With Time-Dependent Rotation Direction And A Rocking Motion The method for mixing in a roller bottle, wherein the controlled axial flow perturbation is introduced by combining a time-dependent rotation direction of the roller bottle with a rocking motion and a time-dependent speed of rotation, which is further defined by a speed of rotation of about 0 to about 50 rpm, and a frequency of rotation direction changes per revolution of about 0 to about 1, rocking angle of about 0° to about +10 degrees or −10 degrees, and a rock to roll frequency of about 0 to about 31.4.

Typical parameters and preferred values are the following: for rotation frequency, 0 to 50 rpm, 0.1 to 5 rpm preferred; for rocking angle. 0 to ±20 degrees, 0 to ±10 degrees preferred; for the magnitude of rotation speed variations, the low speed is 0% to 100% of the high speed, preferred value is when the low speed is less than or equal to 50% of the high speed; for the frequency of rotation speed variations, from 0 to 10 times the frequency of rotation, from 0.05 to 0.5 times the frequency of rotation is preferred; and for the frequency of rotation direction variations, from 0 to 2 times the frequency of rotation, 0.5 is the preferred value.

The instant invention can be understood further by the following examples, which do not constitute a limitation of the invention.

EXAMPLE 1
Development and Experimental Validation of a Computational Model of Fluid and Cell Motion in a Roller Bottle Flow Field Solution The fully three-dimensional flow field for a standard roller bottle was obtained using a commercial CFD software package, FLUENT. The use of FLUENT and similar software packages has been used by several researchers in the past to solve fluid dynamics problems [A. K. Majumdar, R. H. Whitesides, S. L. Jenkins, and D. L. Bacchus, *J. Prop.* 6, 5 (1990); V. Dupont, M. Pourkashanian, A. Williams, and R. Wooley, *Fuel* 72, 497 (1993); J. Seth and W. R. Wilcox, *J. Crystal Growth* 114: 357 (1991); D. Y. Tang, J. J. Ou, R. H. Heist, S. H. Chen and A. J. Dukat, *Ind Eng. Chem. Res.* 32, 1727 (1993); P. D. Swanson, F. J. Muzzio, A. Annapragada, and A. Adjei, *Int. J. Pharm* 142, 33 (1996); and D. M. Hobbs and F. J. Muzzio, *Chem. Eng. Sci.* (to appear 1997).]. The equations of motion for the flow are the well-known Navier-Stokes equations, which, for a two dimensional flow, include the momentum equation in two components and the continuity equation;

$$\partial u / \partial t + u \cdot \nabla u = -\nabla p + (1/Re)\nabla^2 u + (1/Fr) \quad (1)$$

$$\nabla \cdot u = 0. \quad (2)$$

where u is the dimensionless velocity and p is the dimensionless pressure; Re in eq. (1) is the Reynolds number, $Re = \rho vL/\mu$, where $\rho$ and $\mu$ are the fluid density and viscosity, and v and L are the bottle's linear rotational velocity and the liquid height, respectively; and Fr is the Froude number, $Fr = gL/v^2$, where g is gravity. The rationale for selecting liquid height as natural length scale for the flow is that the liquid height is the diffusional length scale in the system. Viscous forces can be viewed as diffusive transport of momentum, with the kinematic viscosity ($\mu/\rho$) playing the role of a momentum diffusivity. Hence, the liquid depth is the natural length scale for the action of viscous forces.

Figure 1A:
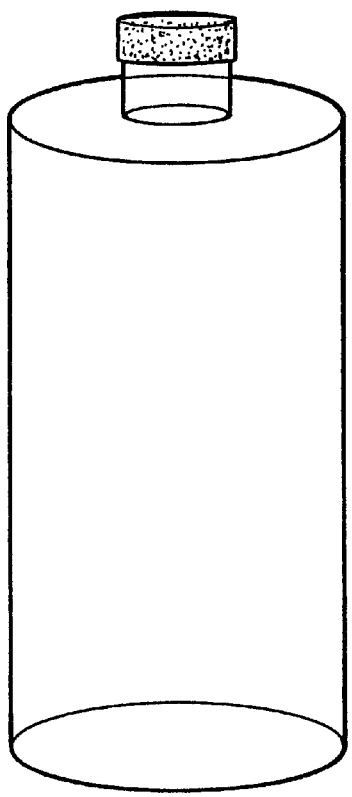
FIG. 1.

The experimental geometry is shown in FIG. 1a. In order to obtain the velocity field, it was assumed that: (a) the flow is steady, (b) the flow is Stokes regime (creeping flow conditions), (c) the free boundary is both planar and horizontal (effects of surface tension and viscous drag on the boundary are neglected). For the conditions used in the biotechnology industry, Re=1, confirming the validity of the creeping flow assumption.

Figure 1B:
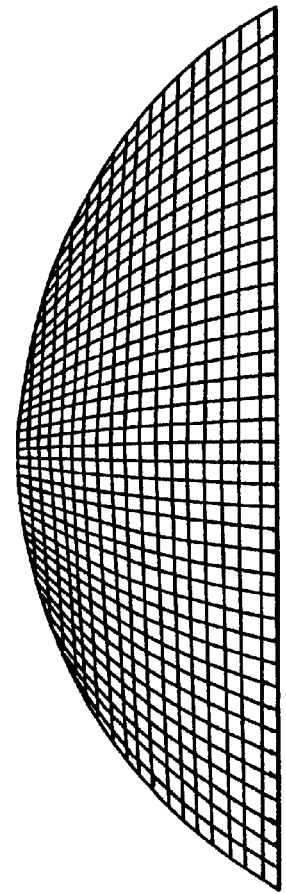

The physical domain was discretized using a curvilinear mesh; while the bottle has a total length to diameter ratio of 2:1, due to the symmetry of the roller bottle, only one-half of the system needed to be simulated, giving a length to diameter ratio of 1:1. The liquid height in the bottle was one-third the total diameter, which was consistent with industrial practice. A 80×20×94 structured computation grid is used; FIG. 1b represents a schematic of the z-plane grid (for the computation a higher node density was used). An acceptable node density for the computational mesh was found by creating several meshes with different node densities. The number of nodes in the mesh was successively increased by 25% until an average velocity difference of less than 3% was achieved for two successive meshes. The lower node density was then used to generate the computational mesh.

Velocity and pressure fields were obtained via iteration using a Sun SPARC 20 workstation. Approximately 140 Mb of RAM and 60 hours of CPU time were need for solution convergence. In order to determine convergence, a criterion of $10^{-6}$ was used for each normalized residual velocity and pressure component. Residuals for each iteration were normalized versus the residual values obtained after the second iteration of the solver. In order to test the sufficiency of the convergence criterion, the simulation was run using convergence criteria ranging from $10^{-5}$ to $10^{-6}$ with no significant change in the velocity field when the convergence criteria was varied over this range (<1.0% change in velocity magnitude, on average). Sensitivity analysis (i.e., trajectory closing) showed that such a mesh is sufficiently accurate. This flow data was then used for all subsequent particle tracking simulations.

The condition adopted in the base case simulation was $\Omega = 0.25$ rpm, giving a Reynolds number of Re=0.3, where $Re = \rho vD/\mu$ and v is the linear rotational velocity, $\rho$ is the fluid density, $\mu$ is the fluid viscosity, and the liquid height is the characteristic diameter, D. At this Re, the flow can be considered to be in the creeping flow regime. The flow was assumed to be sufficiently slow so that it could be assumed that the free surface was always horizontal and no surface tension effects were present at the bottle walls. The free surface was therefore modeled as an impenetrable frictionless wall (i.e. a surface which exerts no stresses on the fluid). Several assumptions were also made regarding the particles (cells). The particles in the flow were sufficiently dilute so that they did not interact with each other or affect the fluid flow in any way. The particles were assumed to be large enough so that Brownian forces could be ignored. All the assumptions used here are valid for the majority of industrial uses of roller bottles.

The Fluid Velocity Field in a Roller Bottle

Two flow visualization experiments were performed in order to validate the simulations. The experiments were done in a glass roller bottle with 10 cm diameter and 20 cm length. The working fluid was glycerin, which had a density of 1.26 g/cm$^3$ and a viscosity of 1.25 Pa s. The bottle was rotated using an apparatus which consisted of a set of rollers whose rotation speed and direction was accurately controlled by a computer. The rotation rate for the two experiments performed was 0.25, giving a Re of 0.04, which is well within the creeping flow regime. The velocity field was first validated via comparison with PIV results. The use of particle imaging techniques to study fluid flow problems is well-documented in the literature and reviewed by R. J. Adrian, Ann. Rev. Fluid Mech. 23, 261 (1991). Information which is pertinent to our specific system is provided here. The flow was seeded with 12 μm diameter silver-coated hollow glass spheres (Potter's Industries) which have a specific gravity of 1.17. A 10 mJ New Wave Research pulsed mini-YAG laser was used as the illumination source. The laser beam passed through a series of optical components to produce a sheet of light 1 mm thick (at a focal distance of 1 m). A 32×32 grid was analyzed using cross-correlation data acquisition, with 10,000 μs between laser pulses. Resultant data from PIV was in the form of velocity direction and magnitude at the center of each interrogation area.

Figure 2A:
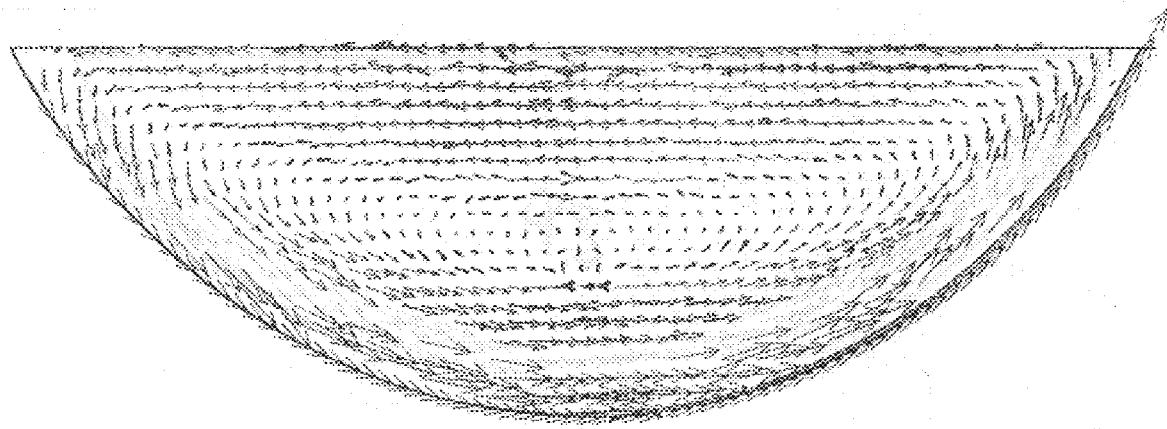

The experimental velocity field was measured at the vertical plane in the middle of the bottle. FIG. 2a,b respectively show the experimental (2a) and computational (2b) velocity vector fields. The length and color of the arrows represent the velocity magnitude in the plane, ranging from low (dark blue) to high (red). As seen in these figures, the velocity fields are qualitatively identical, with the exception of some small experimental scattering near the free surface of the liquid.

Figure 3:
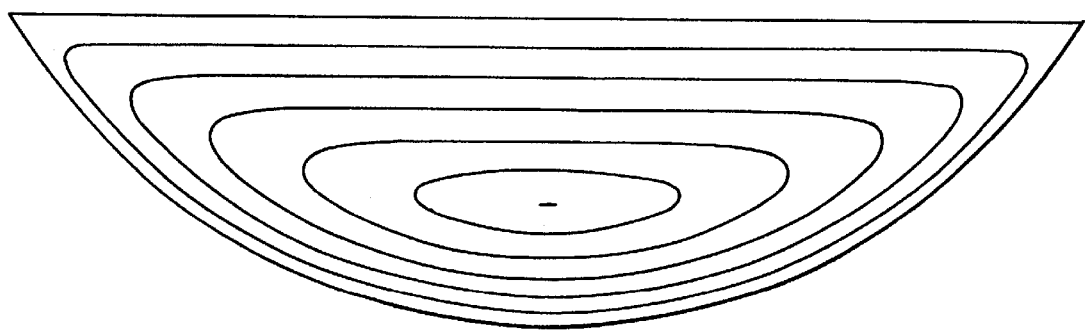
Figure 5:
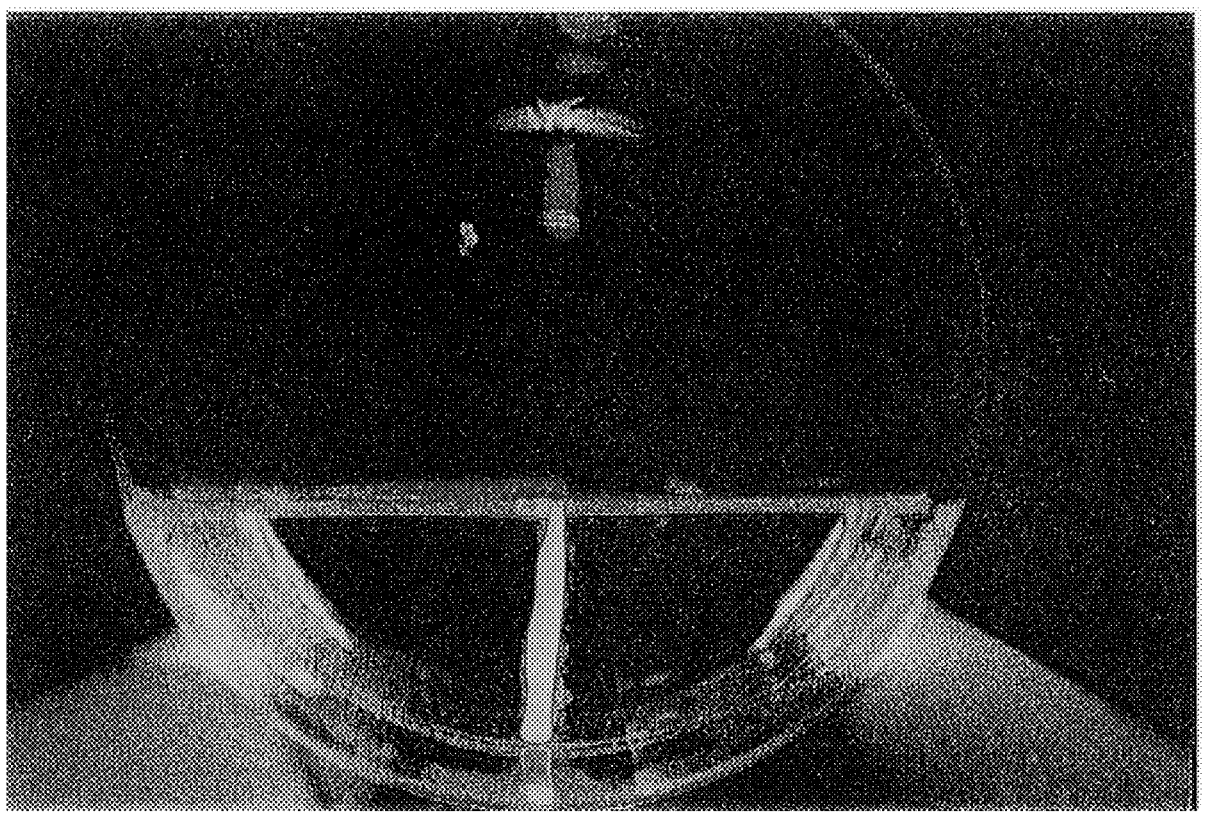
Figure 6:
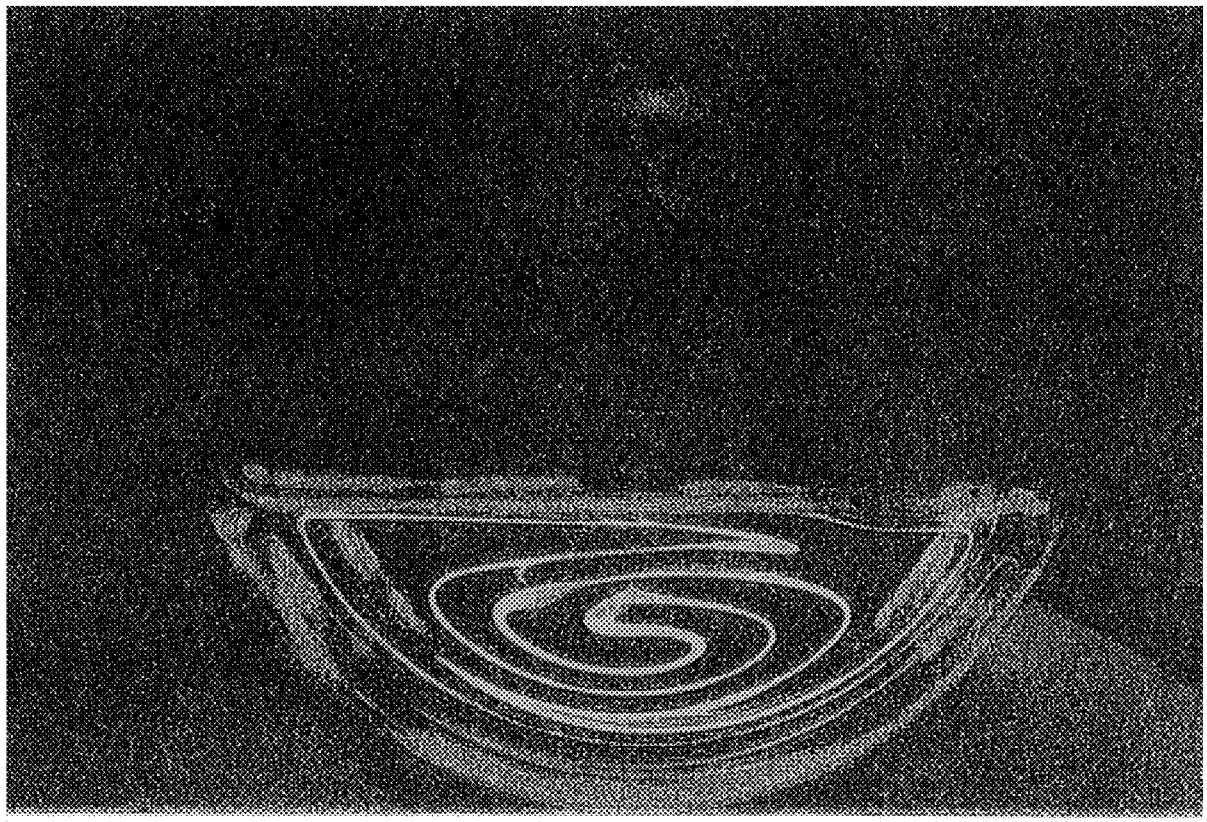

The computational velocity field was further validated by comparing computational and experimental mixing patterns obtained for passive tracers at the center plane of the bottle. This first step for simulating mixing patterns is to determine the trajectories followed by point particles as a result of the equation of motion $$dx/dt = v \qquad (3)$$

where x is the particle position and v is the fluid velocity. FIG. 3 shows the flow particle pathlines predicted using 4th order Runge-Kutta integration of equation (3), which are also the flow streamlines since the flow is steady and the particles follow the flow passively. There is a stagnation point located on the symmetry line at 0.6 unit lengths below the free surface (the unit length is the height of the liquid). A similar approach was used to simulate the evolution of a vertical filament initially placed at the center of the bottle (FIG. 4a). The line consisted of 10,000 particles moving at the flow velocity. FIGS. 4b–4e show the configuration adopted by the line, as revealed by the particle positions, at 4, 8, 16, and 32 bottle revolutions. As the particles are moved by the flow, the line is twisted around the stagnation point. The line stretch in this steady two dimensional flow is linear. The evolution of a fluid line was also observed experimentally in order to verify the simulations. FIG. 5 represents the initial condition, which consisted of a vertical streak of dyed fluid placed in the center plane of the roller bottle, and FIG. 6 shows the evolution of the steak of dye after 20 revolutions. Once again, excellent qualitative agreement between experiments and simulations was obtained, and it was concluded that the simulations indeed provided an accurate representation of the velocity field in the roller bottle.

Once the computational velocity field was validated, it was used to obtain a detailed characterization of fluid motion in the bottle. To provide a clear illustration of a three-dimensional velocity vector field is not a trivial task. In this communication, this is accomplished by using two-dimensional cuts of the velocity field, where the in-plane components are shown using a vector and the total magnitude of the velocity field is shown using color contours, with red signifying high velocity and blue indicating low velocity.

Figure 2B:
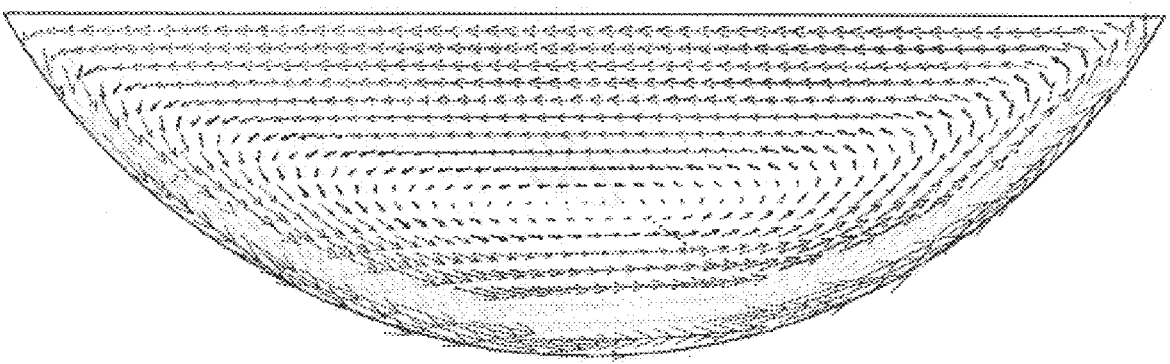

FIG. 7 shows vertical cross-sections at 2 cm intervals through the bottle (i.e. z=0.0 is 0.0 m from the end wall, and z=0.1 m is at the symmetry plane in the center of the roller bottle). FIG. 7f corresponds to the center of the bottle and is therefore identical to FIG. 2b Moreover, FIGS. 7d and 7e are also identical to FIG. 7f, indicating that end effects play little or no role in the fluid flow past 5 cm from the end of the bottle. The velocity field shows both especular symmetry relative to the center plane (expected from the symmetry of the boundary) and anti-symmetry between the left and right sides of the bottle (expected from the creeping flow condition and the rotational symmetry of the bottle). As discussed below, this observation can have important implications, because the flow induced by the ends of the bottle is the only means of axial mixing.

Figure 7A:
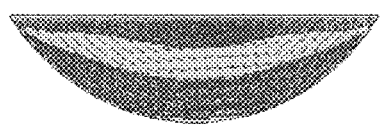
Figure 7B:
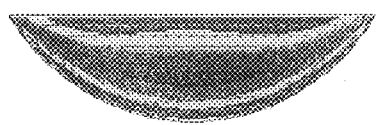
Figure 7C:
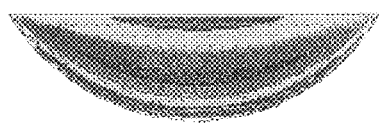
Figure 7D:
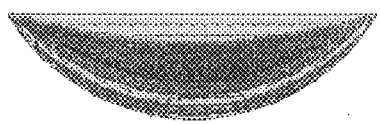
Figure 7E:
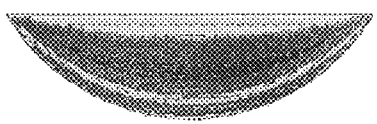
Figure 7F:
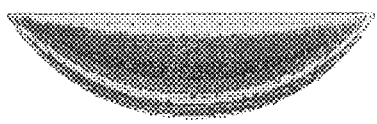

FIG. 7a represents the velocity field at the end of the roller bottle. Due to the no-slip condition at the bottle wall, all fluid follows the bottle wall in a counter-clockwise direction. When the fluid reaches the free surface (at the right side), it detaches from the wall and flows outward in the z-direction. At the left side, the fluid immediately adjacent to the wall is drawn downward; this motion is "fed" by an inward flow from the z-direction. FIGS. 7b and 7c show the presence of a high velocity component near the surface of the liquid, caused by the end effects. However, detailed examination of the velocity vectors displayed in FIG. 7b–c indicate that the x and y components of the velocity field are largely unaffected by end effects; such effects appear primarily in the axial (z) component of the velocity field.

Figure 8:
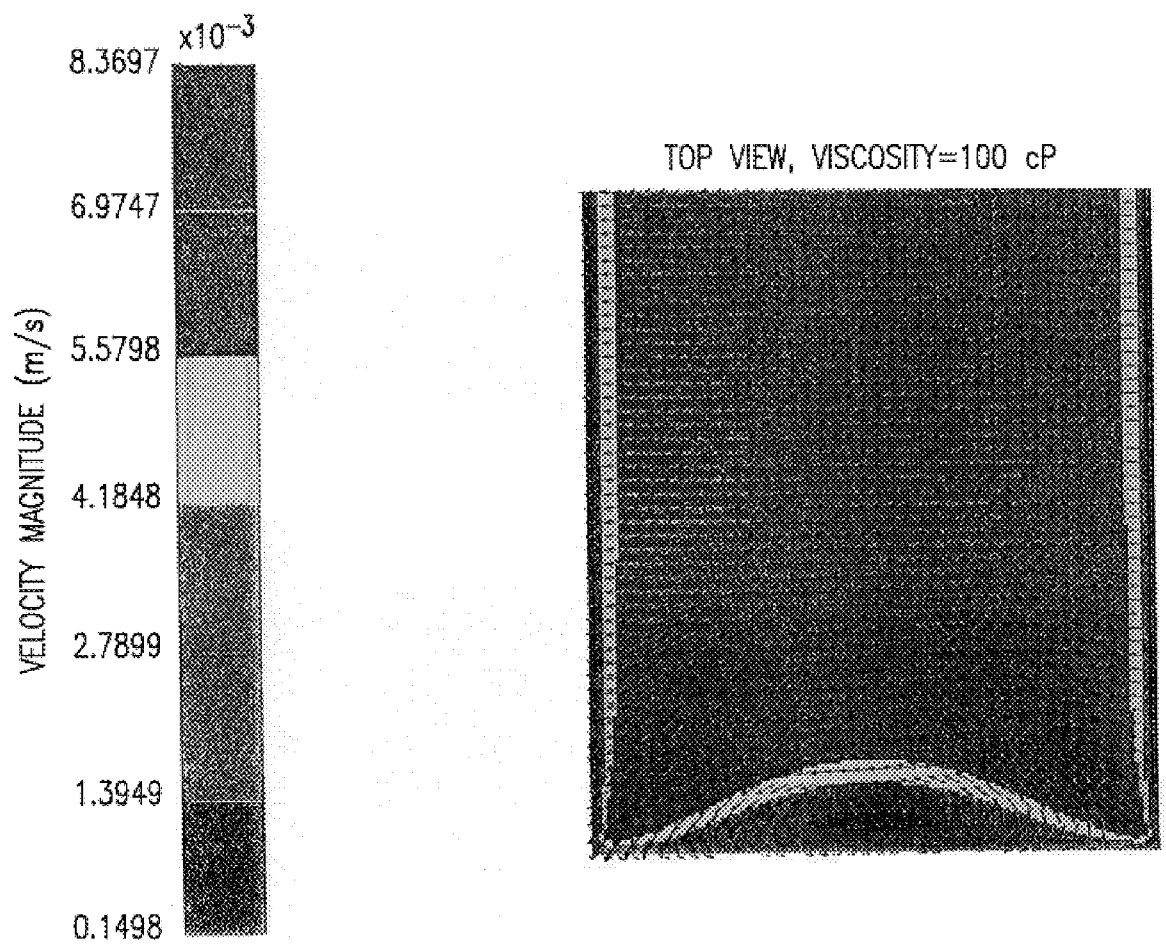

The end-wall effects are more clearly shown by a top view of the bottle. FIG. 8 shows a velocity contour plot just below the liquid free surface. The end of the bottle is at the bottom of this figure, and the symmetry plane is at the top. Flow in the axial (z) direction is clearly visible in this figure. The fluid flows upward from the end wall in the lower right-hand corner travels in a counter-clockwise loop, then flows downward at the lower right-hand corner due to the end-wall flow. There is a stagnation point 0.46 cm from the end of the bottle, as shown in the dark blue color. Moving toward the center of the bottle, end effects have less effect on the flow; there is less than 2% difference in the velocity field between the 2-D symmetry plane and the plane at 5 cm from the end wall. The surface flow in this region is from right to left.

Figure 9:
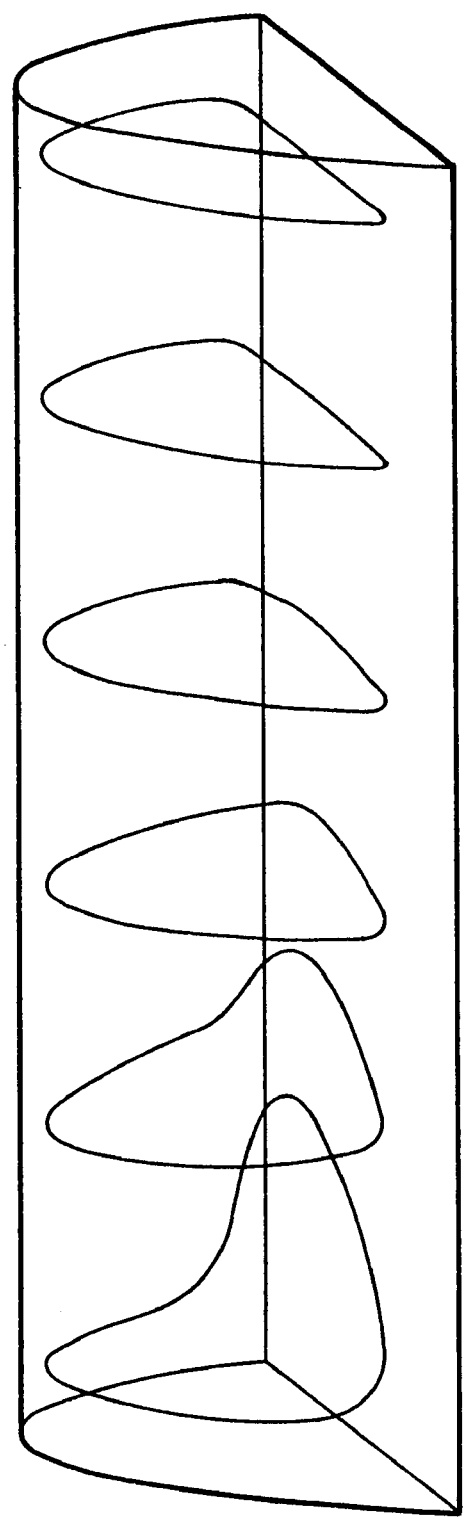

An alternative illustration of the three-dimensional flow pattern in the roller bottle is obtained by computing the pathlines of the flow. FIG. 9 shows six pathlines for fluid particles initially placed 0.2 cm from the bottom of the bottle. The center of the bottle is at the left-hand side of the figure, and the end wall is at the right. Looking at the pathlines from left to right, we see the effect that the end wall has on the flow field. The pathline at the center plane is a two-dimensional vertical loop identical to the pathlines observed in FIG. 3. As we move toward the end of the bottle, the pathlines begin to bend near the free surface toward the center of the bottle. All the pathlines shown are closed loops. The pathlines at the center plane of the bottle are two-dimensional loops, and the pathlines away from the symmetry plane are three-dimensional loops. In either situation, however, the same result ensues: fluid particles in the flow remain trapped in the closed periodic orbits and do not contact other portions of the flow. Such regular motion patterns indicate that fluid mechanical mixing in this flow is very poor and that homogeneization occurs primarily by diffusion. Experimental evidence of this observation, and approaches for overcoming mixing limitations, are discussed below.

The Motion of Cells in a Roller Bottle

The modeling of small but finite particles in the flow field was carried out by using as a starting point the proposed by Maxey and Riley [M. R. Maxey and J. J. Riley, *Fluids* 26, 883 (1983).]:

$$m_P \frac{dv}{dt} = (m_P - m_F)g + m_F \frac{Du}{Dt} - 6\pi a^2 \mu \int [\pi v(t-\tau)]^{-1} \left(\frac{dX}{dt}\right) d\tau - \quad (4)$$

$$\left(\frac{1}{2}\right) m_F \frac{d[u - v - (1/10)a^2 \nabla^2 u]}{dt} - 6\pi a^2 \mu X$$

$$\text{where } X = u - v - \left(\frac{1}{6}\right) a^2 \nabla^2 u$$

In these equations, u is the fluid velocity vector, v is the cell velocity vector, a is the cell radius, v is the fluid kinematic viscosity; $m_p$ and $m_F$ respectively correspond to the weigh of the cell and that of the fluid displaced by the cell. The five terms in the right hand side of the equation correspond to buoyancy forces, pressure forces, flow history effects, added mass effect, and Stokes drag forces. This equation can be significantly simplified for the roller bottle problem. Since u is known from the numerical solution of the flow, the relative magnitude of each term can be evaluated. Analysis has shown that the leading order terms are inertia, buoyancy, and drag forces, thus the equation becomes:

$$\frac{dv}{dt} = Gg + \frac{1}{S_{tk}}(u - v). \quad (5)$$

where $$G = 2(\gamma - 1)gL/[(2\gamma + 1)U^2],$$

and $$S_{tk} = (2\gamma + 1)a^2 U/(9vL);$$

γ is the particle density relative to the fluid density, L is the depth of the fluid, and U is the bottle rotation velocity. If we assume that the particles are cells and the rotation speed and liquid are typical of those used in the biotechnology industry, this equation can be further simplified. A typical example is that $$G \sim O(10^{+3})$$

and $$S_{tk} \sim O(10^{-6}).$$

Figure 10:
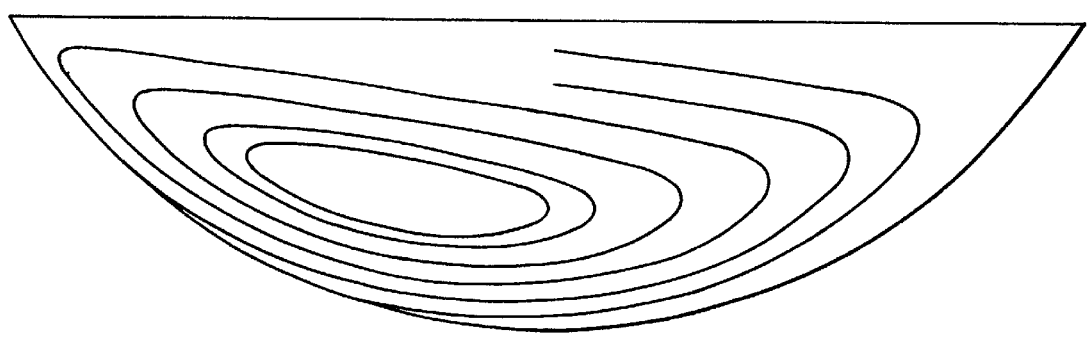

This allows the inertia term to be neglected, greatly simplifying the problem. The particle velocity is obtained immediately as $$v = u + V_s, \quad V_s = \frac{2a^2(\gamma - 1)}{9vU}g. \quad (6)$$

where v, the total particle velocity, is simply the sum of u, the fluid velocity, and $V_s$, the particle terminal settling velocity. Once v is known, particle positions are found by numerically integrating the equation, $$dx/dt = v \quad (7)$$

using the standard 4th order Runge-Kutta method. In order to understand the small particle behavior in a steady rotating roller bottle, equations (6) and (7) are used to simulate the motion of particles on the center plane of the bottle. FIG. 10 shows the particle trajectories for a settling velocity $V_s = 0.05U$, where U is the nondimensional tangential velocity of the bottle wall. Six particles were initially placed on the vertical center line. The particles showed different behaviors: while the two particles nearest to the free surface reached the rotating wall in a fraction of a bottle rotation, the remaining four particles moved in closed orbits. Such particles will never reach the bottom wall. This simulation indicates that whether a particle settles or not depends not only on its settling velocity, but also on its initial location within the flow field. Moreover, since the settling velocity used in this simulation is much larger than those corresponding to real systems, FIG. 10 actually indicates that a substantial fraction of the cells in a roller bottle could actually remain trapped indefinitely in recirculating trajectories within the bottle flow, never reaching the bottle wall.

Figure 11:
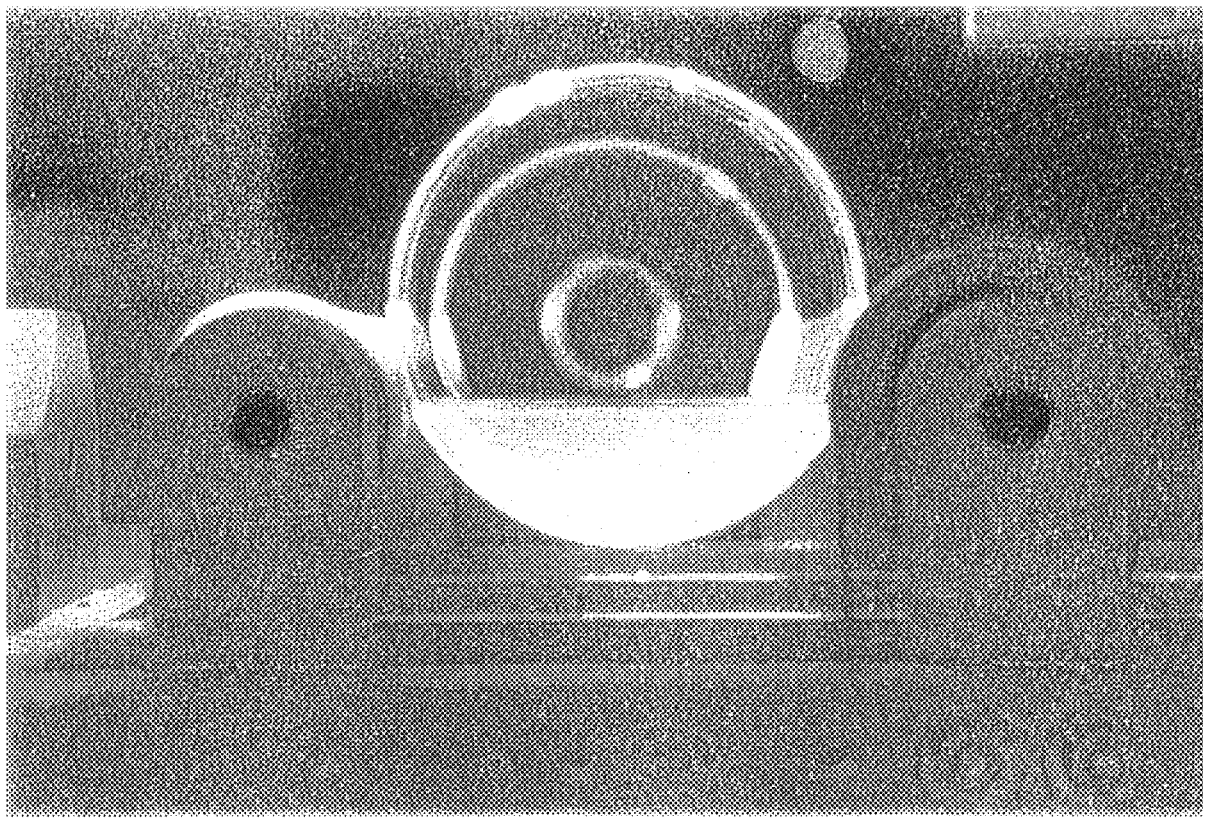

This simulation result was investigated experimentally by using long-exposure-time photography to reveal the pathline followed by a fluorescent particle with a settling velocity similar to the one corresponding to FIG. 9. A 200 μm fluorescent polystyrene particle was placed in the center plane of the roller bottle. The particle had a terminal settling velocity of approximately 0.5 cm/min, or 0.06 U, where U is the linear rotation velocity of the roller bottle. Using long-exposure L photography, the particle pathline was photographed for one bottle revolution under fluorescent light. Results from such an experiment are shown in FIG. 11. The original position of the particle was approximately 0.6 length units from the free surface (where the unit length is the height of the fluid). The pathline revealed in FIG. 11 closely resembles the pattern shown in FIG. 10, which is a simulation for particles of roughly similar settling velocity. When the particle was originally placed in a different location, closer to the bottle center, the particle followed a different closed pathline. When placed close enough to the upper surface, the particle eventually settled and remain attached to the bottle wall.

Detailed Analysis of Cell Settling: Particle Settling Results

Figure 12:
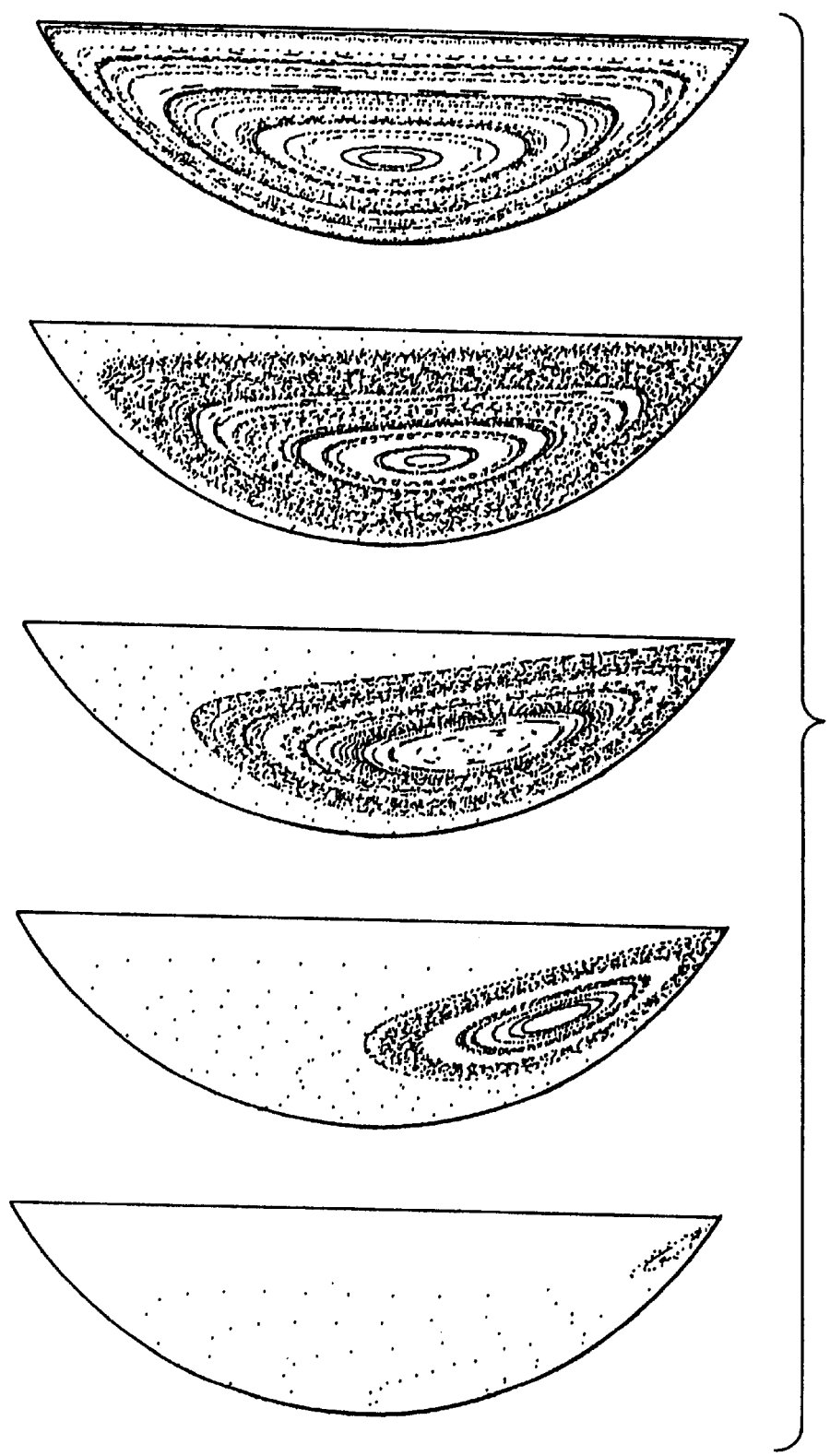

A more complete picture of cell behavior can be obtained by following a large number of cells over a long period of time. Such simulations were conducted by placing 20,000 particles uniformly distributed across the entire central cross-section of the bottle, and following them for 20 rotations of the bottle. Whenever a particle touched the bottle wall, it was (arbitrarily) assumed that the particle had "settled" and was removed from the simulation. FIG. 12 shows the final positions of particles obtained form such a simulations for settling velocities $V_s=0$, 0.02U, 0.05U, 0.1 U, and 0.2U. For these simulations, the bottle was rotating counter-clockwise at a non-dimensional linear velocity of U=1.0. For $V_s=0$ (FIG. 12a), the structure of the particle positions is identical to those of the flow streamlines since such particles are in fact fluid particles. Particle positions form closed orbits, indicating that all particles are confined inside closed orbits. As expected, no settling occurs in the flow. As $V_s$ increases, the particle paths are perturbed away from streamlines, but as it is shown in FIG. 12b, for $V_s=0.02U$ most particles remain trapped in closed periodic orbits and never reach the walls; only those particles initially very close to the free surface and the bottle wall are able to reach the bottle boundary. As settling velocity increases, more particles settle, but only for large values of $V_s$ (i.e., $V_s=0.2U$, FIG. 12e) are most particles able to reach the bottle walls.

Figure 13A:
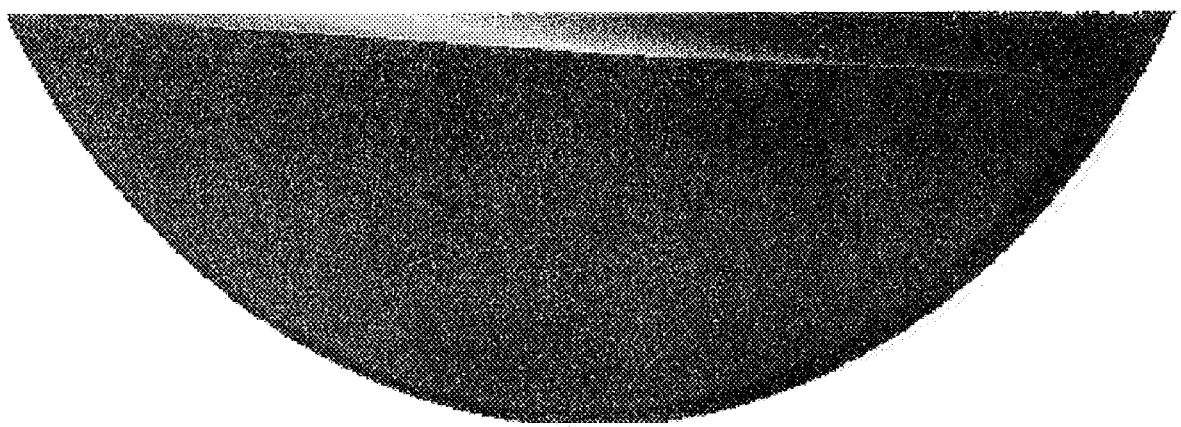
Figure 13B:
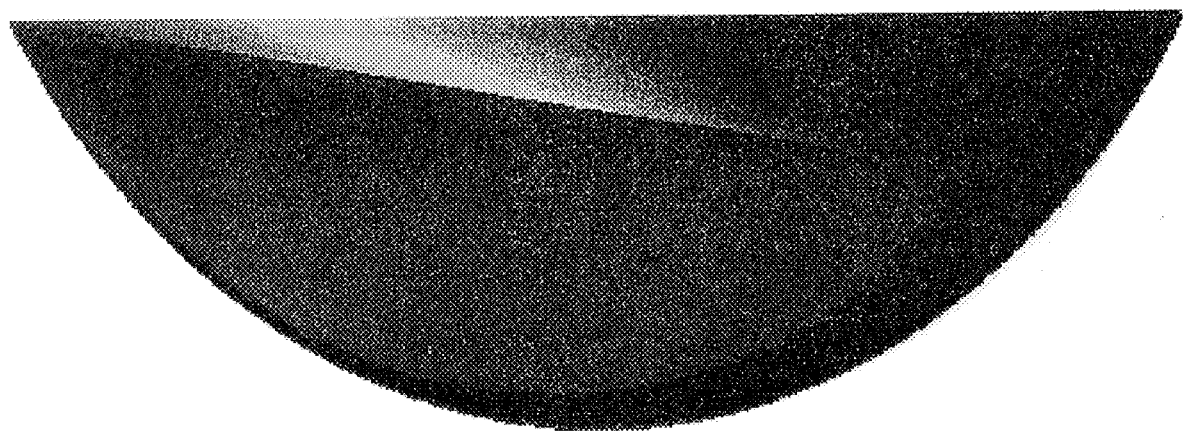
Figure 13C:
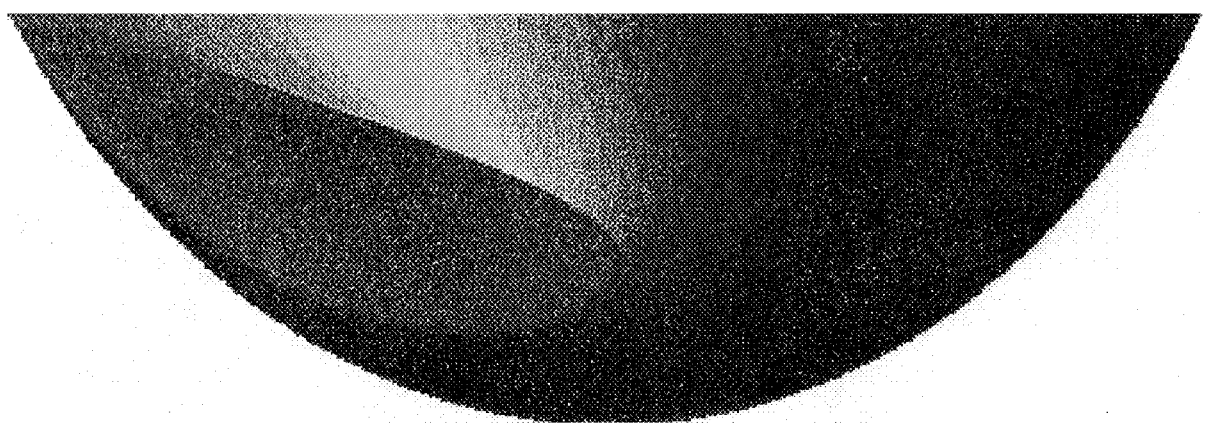
Figure 13D:
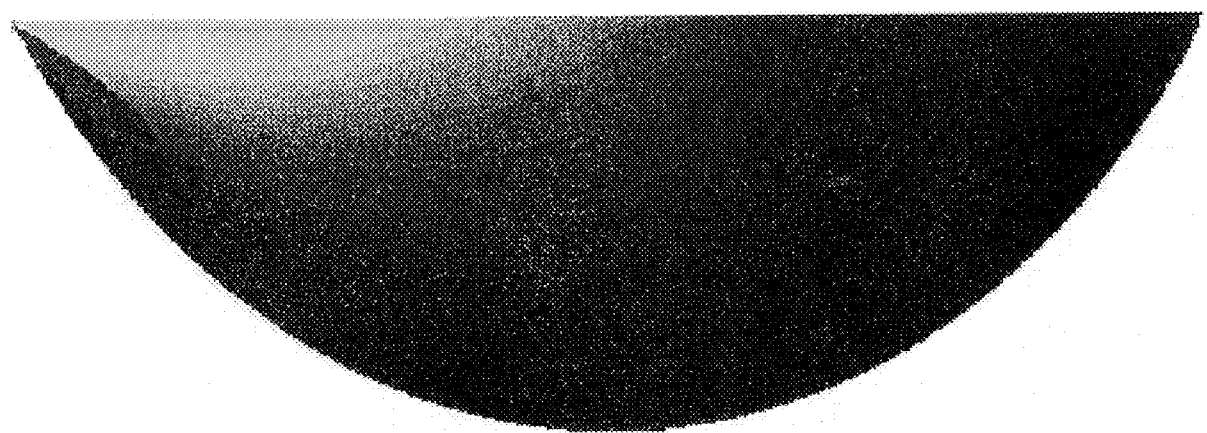

Although such simulations give information about the dynamical behavior of particle motion, the settling rate can not be inferred from them. In order to obtain the spatial distribution of particle settling times, the settling time of each particle was recorded and plotted as a function of initial particle location. The settling time distribution in the bottle is shown in FIG. 13. The bottle is rotated clockwise at a nondimentional linear velocity of U=1.0 at the wall. Results correspond to $V_s$=0.02 (FIG. 13a), 0.05 (FIG. 13b), 0.1 (FIG. 13c) and 0.2 (FIG. 13d). The colors from dark blue to red represent the particle residence time from 0 to the maximum computing time. The smooth core region in red represents the particles that do not settle at all. For small $V_s$=0.02 (FIG. 13a), only a narrow stripe of particles under the top free surface and near the bottom on the right side of the bottle settle. The width of this strip increases as $V_s$ increases and the size of the red core decreases. The tip of this core region is always at the upper left corner of the flow and leans to the left bottom of the bottle. At $V_s$=0.1 (FIG. 13b), the particles in the majority region of the bottle will settle. When $V_s$ is increased to 0.2 (FIG. 13c), almost all the particles settle to the wall. The spatial distribution of particle settling time in the flow is shown clearly by the color shades. Short lived particles are always on the right side of the bottle for this flow direction. If the flow direction is reversed, FIG. 14 would appear as a mirror image of itself due to the symmetry of the system. These results clearly reveal that the particle residence time distribution is strongly affected by the recirculation of the flow.

Figure 14:
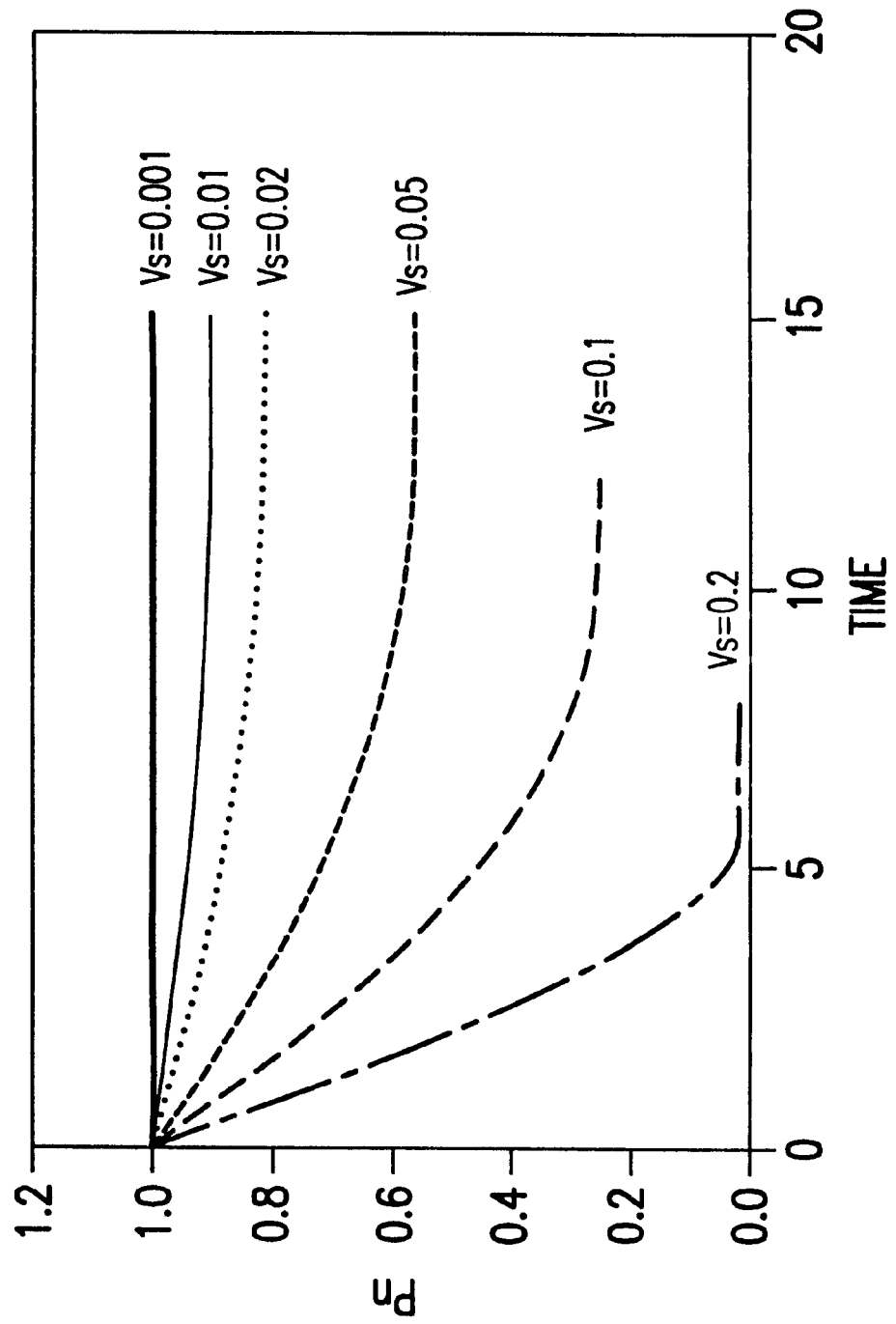

The rate of particle settling is shown in FIG. 14. In this figure, the number of particles suspended in the flow at a given time is plotted against time. From this figure, it can be seen that all the settling processes are nonlinear (except perhaps for $V_s$=0.2). Particles settle to the wall relatively fast at the initial stage, and then the rate of settling (the slope of the curves) levels off in a relatively short time, about 8 to 12 time units. With large settling velocity ($V_s$=0.2, the heaviest particles examined), the particles settle at almost a constant rate.

EXAMPLE 2
Enhancement of Cell Deposition by Perturbation of Rotation Direction
Using Unsteady Rotation to Enhance Settling Comparison of FIG. 3 and FIG. 12 indicate that the non-settling behavior is caused by the strong recirculation present in the flow, which in two-dimensional cuts of the flow field causes the flow to behave as sets of nested closed loops. When a particle is in the lower part of the flow (below the stagnation point), it falls through loops toward an outer loop. However, if the particle does not reach the wall, it then moves to the upper part of the flow, and then falls toward an inner loop. Combination of these two effects causes the particle to move up Once the acidic glycerin was injected back into the roller bottle, the mixer was turned on and the bottle was rotated at constant speed. FIGS. 21a–c show the results of this experiment. The initial condition is shown in FIG. 21a, mixing after 32 revolutions is shown in FIG. 21b, and mixing after 64 revolutions is shown in FIG. 21c. These figures clearly reveal the effect of the symmetry plane located in the center of the bottle. After 32 revolutions, mixing within each half of the bottle is complete. This mixing is caused by the axial motion of fluid due to the end-wall effects. However, even after 64 bottle revolutions, there is minimal mixing between the two halves of the bottle; neutralization of the base on the right-hand side will occur only through the action of diffusion.

Recent experiments dealing with mixing of dry powders in a rotating and rocking cylinder have shown that a small-amplitude rocking motion in the vertical direction can greatly enhance mixing in the axial direction [C. Wightman, P. R. Mort, E. K. Gleason and F. J. Muzzio, *Powder Tech.* 84:3, 231 (1995).]. This approach was implemented here to attempt to enhance mixing in the roller bottle. Two conditions were examined: (a) mixing at a rocking frequency of 1.6 bottle revolutions per rocking cycle, and (b) mixing at a rocking frequency of 3.2 bottle revolutions per rocking cycle.

FIGS. 21d–f represent the effect of rocking on mixing in the system. The roller bottle was rocked approximately 12 degrees at a rocking rate of 1.6 bottle revolutions per rock. It can be seen that mixing is improved substantially in the system as a result of the rocking. Similarly, FIGS. 21g–i represent mixing for a rocking rate of 3.2 bottle revolutions per rock. These results demonstrate that rocking indeed enhances mixing, which is essentially complete after 64 revolutions. Moreover, since rocking disrupts the recirculating flow patterns described above, it is also likely to disrupt cyclical cell motions and enhance settling. It is important, however, to realize that if rocking were to be used to enhance mixing in a cell growth process, the choice of rocking frequency and amplitude should take into account the need to keep the cells submerged in the nutrient medium as uniformly as possible. If one chose an integer number of revolutions per rocking cycle then the cells at the top of the bottle when the rocking reached it maximum angle of inclination would always be the same and they would be exposed to nutrients for a substantially shorter fraction of time than those at the bottom. The rocking frequencies of 1.6 and 3.2 revolutions per rocking cycle were chosen because these frequencies should keep the cells fairly uniformly exposed to the nutrients, although the cells closer to the neck of the bottle will still be exposed less to the nutrients.

EXAMPLE 4
Effects of Bottle Rotation Speed on Cell Culture Experiments: Time Dependent Speed of Rotation Frozen MRC-5 cells were thawed, and the cells were cultivated in either T-flasks or Nunc Cell Factories, which are flat, stationary growth surfaces. The cells attached to and propagated on the lower surfaces of these containers, where they were submerged under a nutrient growth medium. Every 6 days, the cells were removed from the surface by enzymatic means, known as trypsinization. The resulting cell suspension was then diluted and placed into a larger number of vessels for further propagation.

On day 27 of the process, the freshly trypsinized, concentrated cell suspension was then placed in the roller bottles along with 125 mL of growth medium. The bottles were rotated at 0.25 rpm or 0.5 rpm and incubated at 37° C. An additional 300 mL of growth medium was added to the bottles on day 33. As shown below, the higher rotation rate resulted in higher cell yields. The figures represent the average number of cells yielded per bottle on day 35 of the process. This represents a 23%±10% increase in cell number over the 0.25 rpm rate of rotation.

| Trial | MM Cells/PB | |
|---|---|---|
|  | 0.25 RPM | 0.50 RPM |
| 1 | 64.3 | 88.3 |
| 2 | 60.4 | 75.6 |
| 3 | 75.3 | 92.6 |
| 4 | 56.1 | 66.3 |
| 5 | 65.2 | 71.5 |
| Mean | 64.26 | 78.86 |

Figure 18:
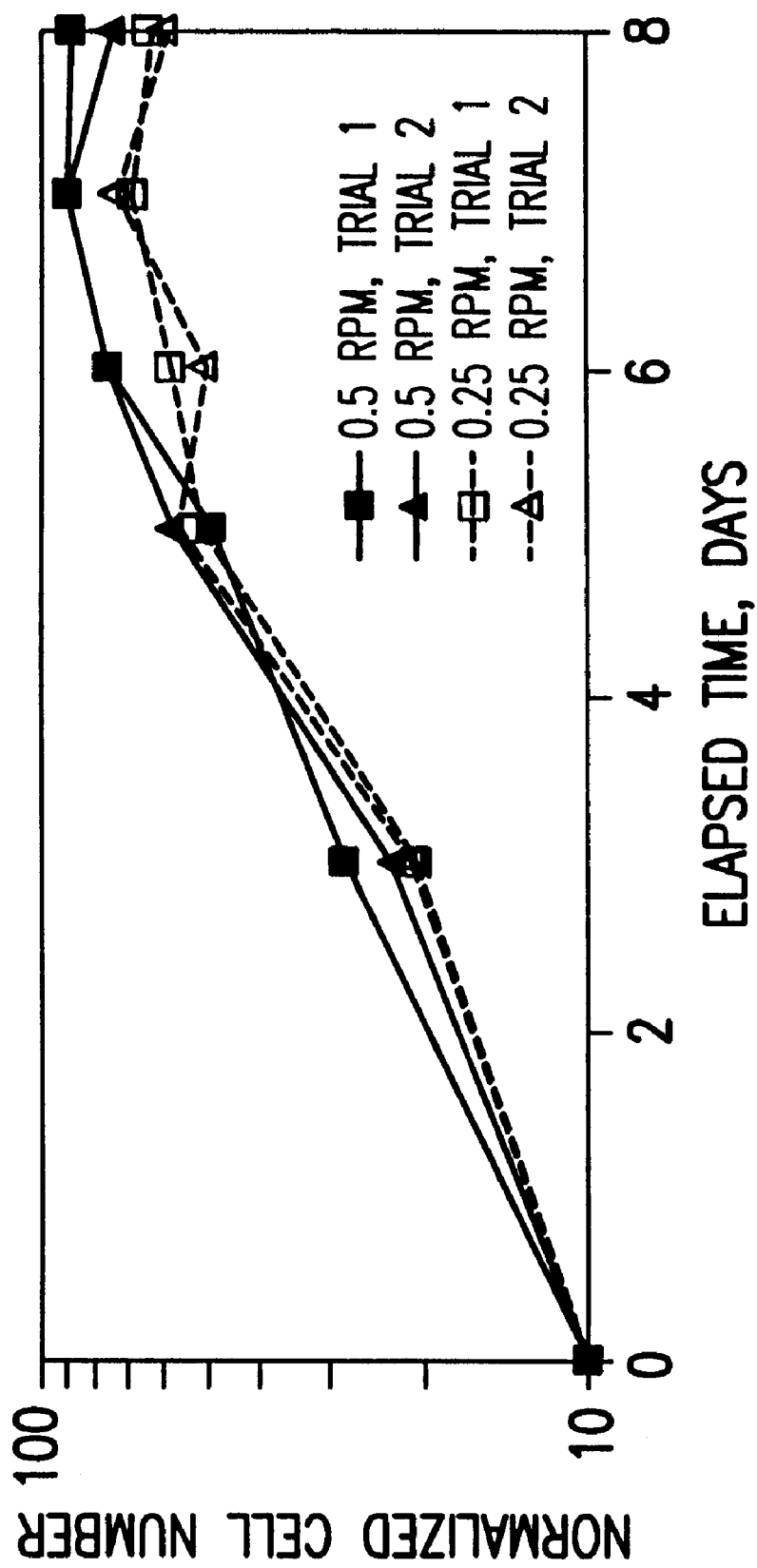
Figure 19:
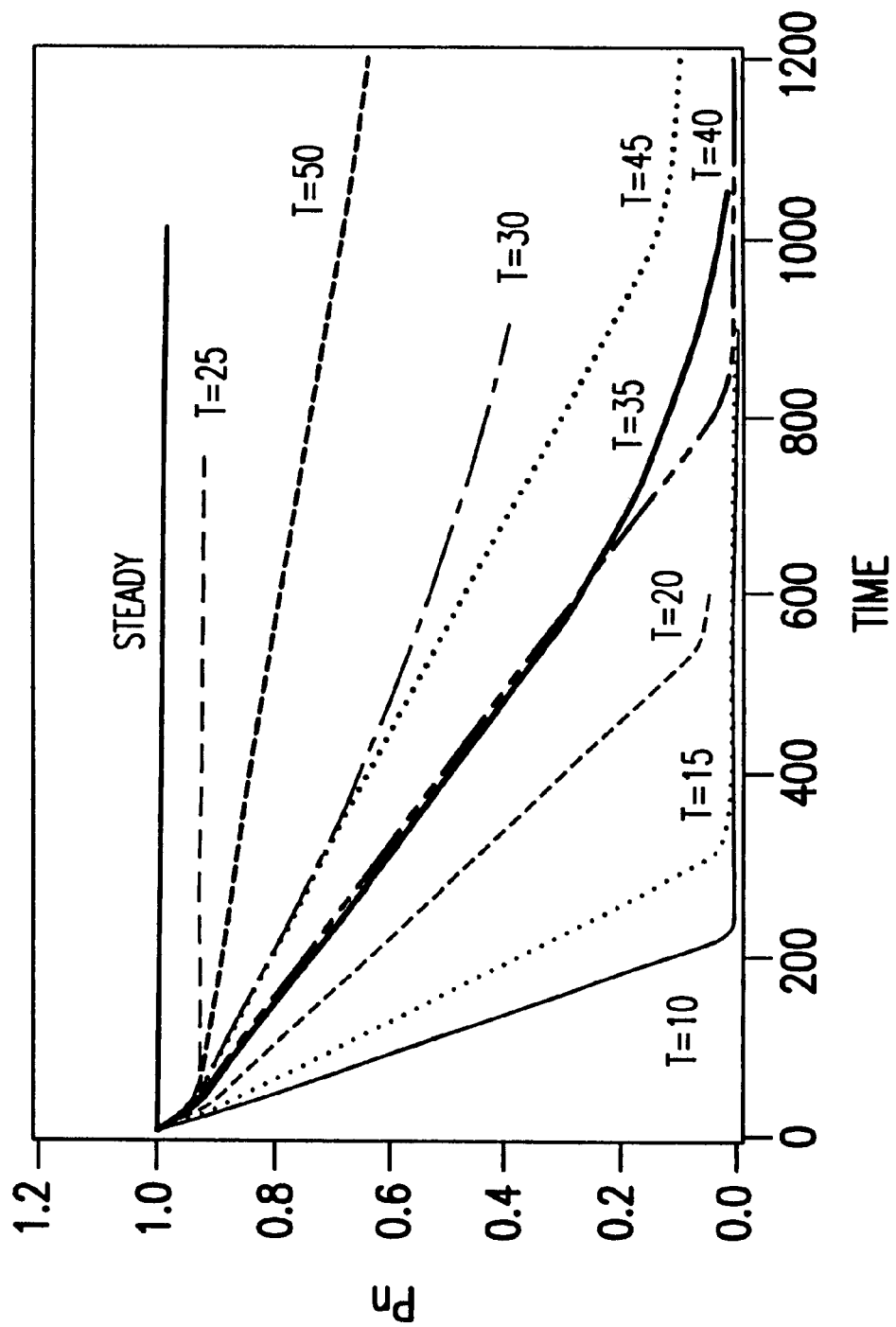
Figure 20B:
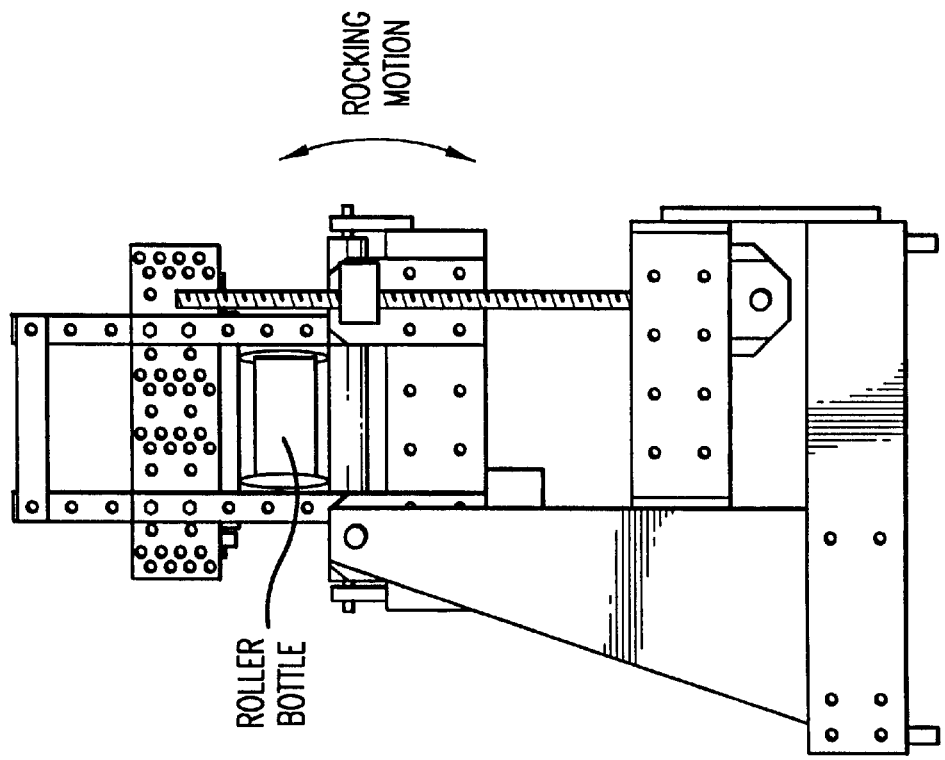
Figure 20A:
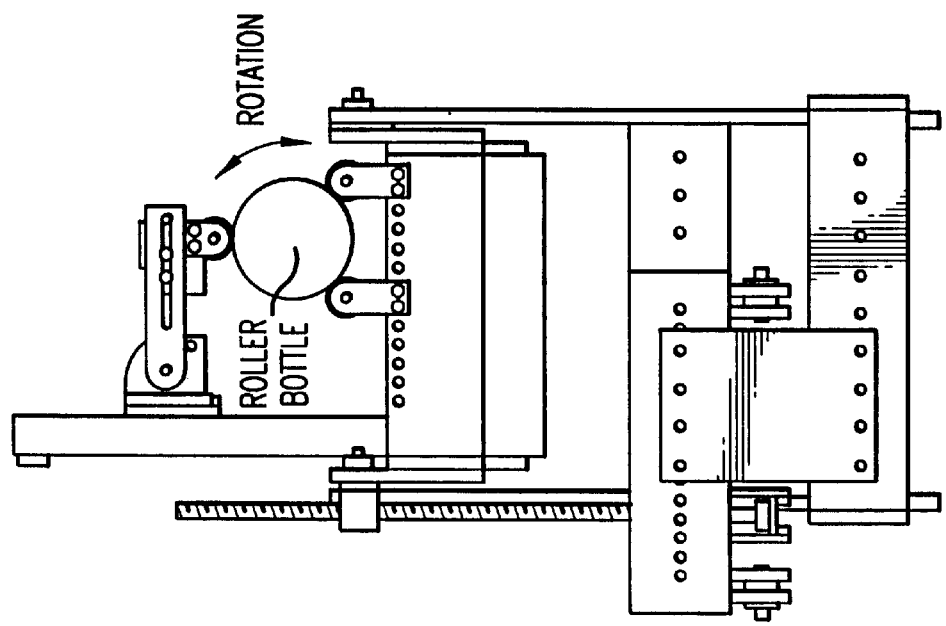

The higher cell yield is obtained by a prolongation of the exponential growth phase. See FIG. 18, which depicts the daily growth curves for two of the five trials. The figure illustrates that the higher cell numbers are not due to a higher growth rate, rather the exponential growth phase of the culture has been extended. This may be attributable to improved transport of nutrients, gases, and waste products resulting from the faster rotation.

EXAMPLE 5
RPM Changes Result In Higher Productivity

Roller bottle cultures from Trials 4 and 5 above were then infected by the addition of freshly trypsinized, virus-infected MRC-5 "working seed" cells. The virus infected cells were added to the liquid nutrient medium in the roller bottle, where they attached to the uninfected cell monolayer which had been established on the inside surfaces of the roller bottle. Once the bottles were inoculated with the "working seed", they were rotated at alternate rates.

The table below describes the normalized results from the experiments.

| Rotation Rate, rpm | | | | | |
|---|---|---|---|---|---|
| Day 27–Day 35 (Cell Growth) | First 6 Hours of Infection on Day 35 | Remainder of Infection Period | Average Normalized Titer | Standard Deviation | 95% Confidence Interval |
| 1/4 | 1/4 | 1/4 | 1.00 |  |  |
| 1/4 | 1/8 | 1/4 | 1.04 | 0.28 | 0.15 |
| 1/2 | 1/4 | 1/4 | 1.15 | 0.30 | 0.16 |
| 1/2 | 1/8 | 1/4 | 1.32 | 0.30 | 0.16 |

The potency was evaluated by five replicate plaque assays for each of the four experimental groups, for each of the two experiments. The combination strategy of the faster rotation for cell growth and slower rotation for the initial period of infection resulted in 32% more product, with a 95% confidence interval of 15%, indicating a statistically significant result.

As mentioned earlier, the rotating bottle creates circular liquid flows, in which the varicella-infected cells can become "trapped." As these infected cells circulate in the liquid phase, they gradually lose their infectivity (the ½-life of the infectivity is less than 5 hours). Although slowing the rotation rate of the bottles does not break up the circular flows, modeling had shown that it would allow more of the trapped cells to reach the surface sooner via settling, as borne out by these experiments.

Transport of Virus-Infected Cells to the Roller Bottle Surface

Figure 15:
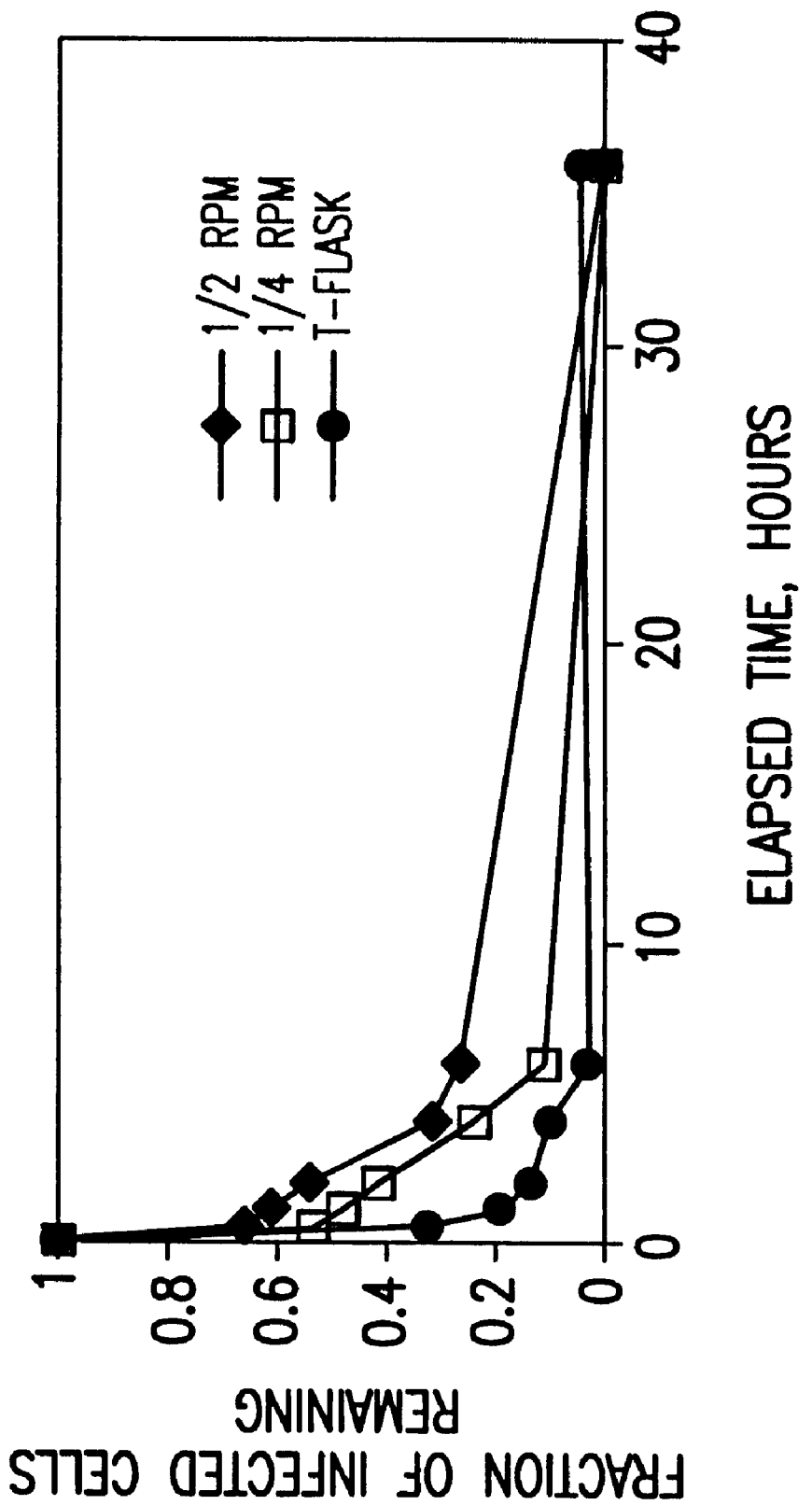
Figure 16:
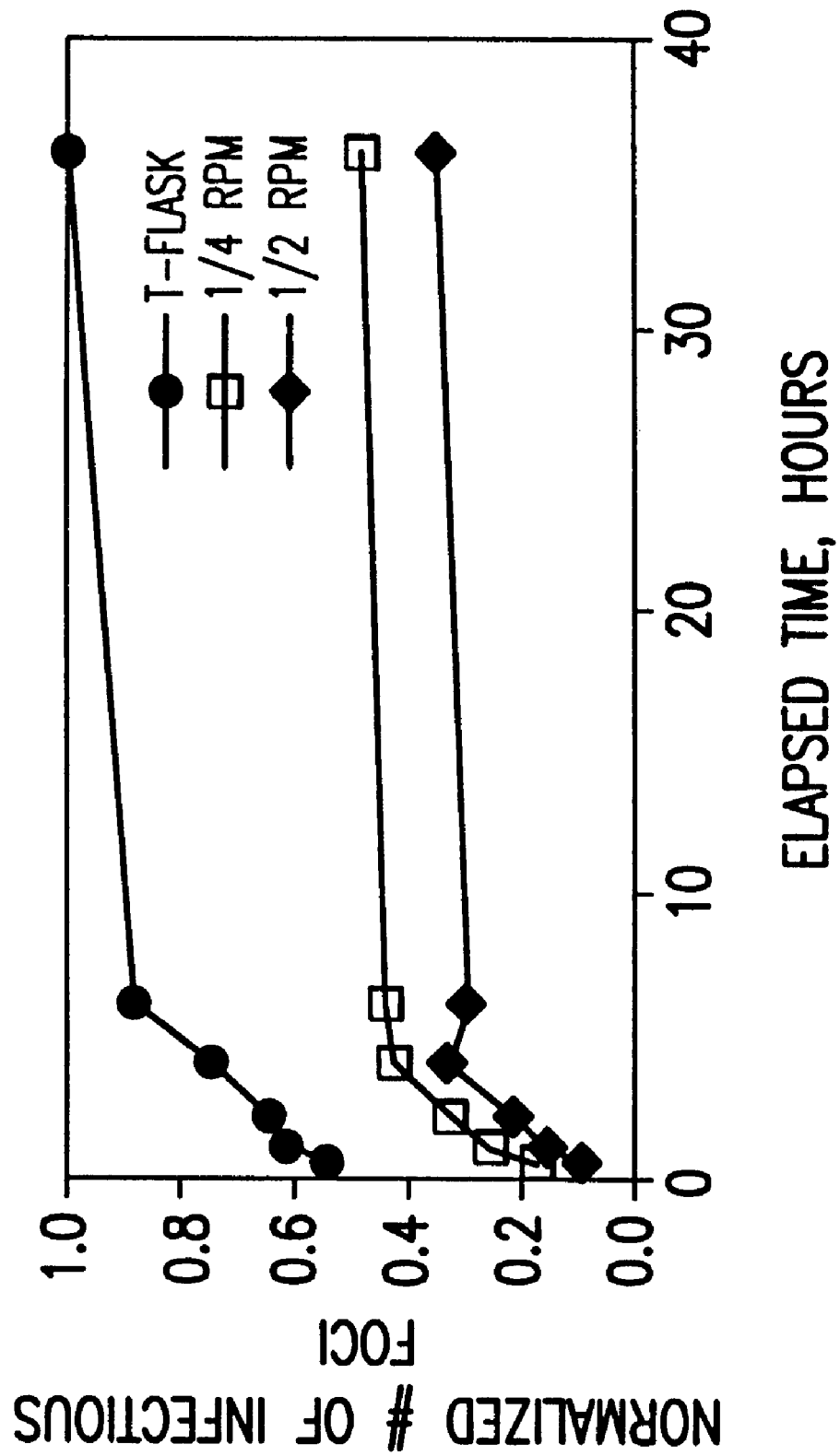
Figure 17:
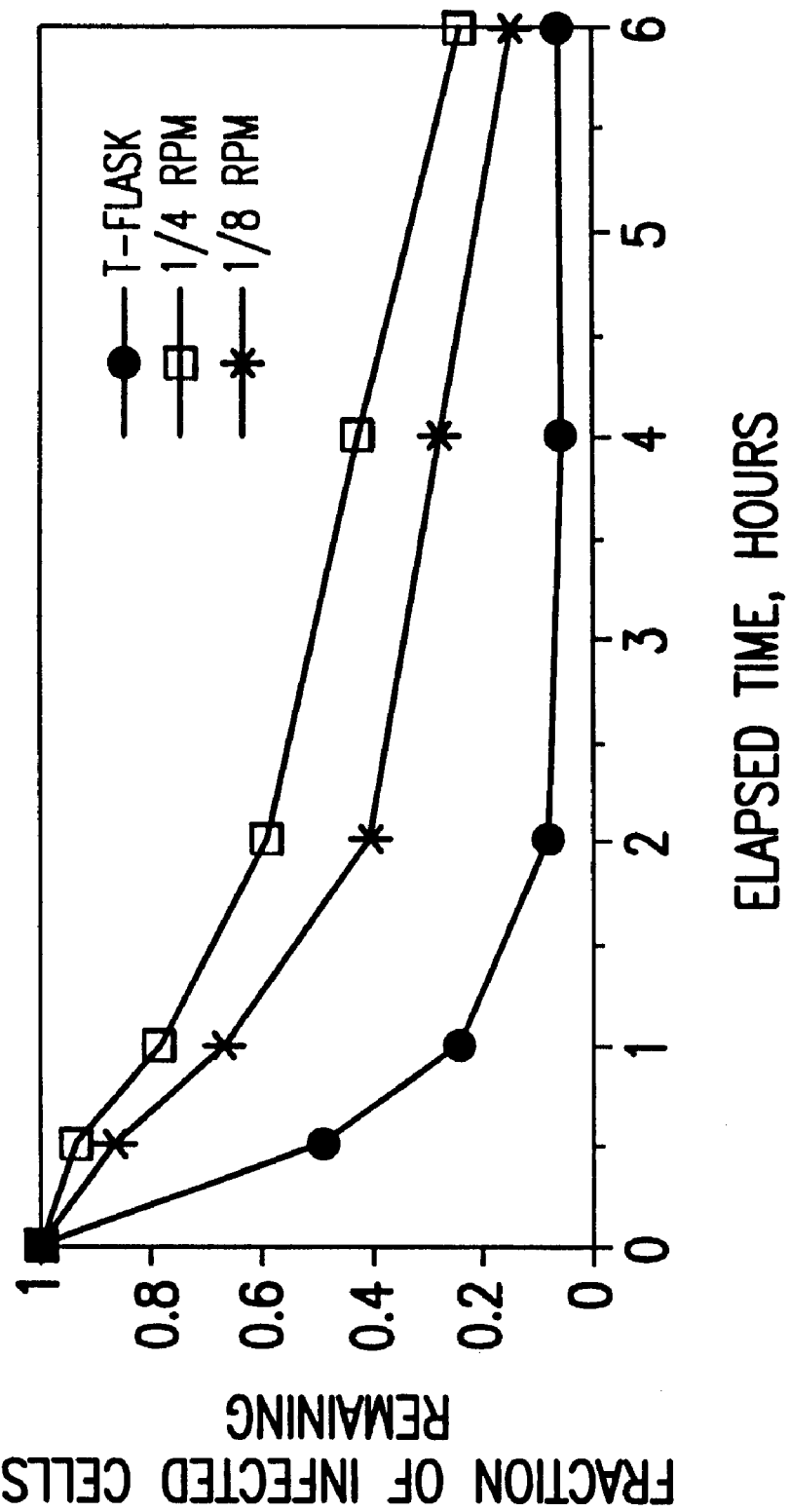

FIGS. 15 through 17 illustrate that a slower rotation rate results in faster transport of infected cells to the cell culture which has been established on the inner surfaces of the roller bottle. It is important to minimize the length of time which the infected cells spend in the culture supernatant for two reasons. First, time in the supernatant is process time during which a given virus-infected particle is not infecting the cell monolayer, and thus, generating product. Second, the half life of the virus activity less than 5 hrs. Time spent in the supernatant translates directly into degraded viral material.

FIGS. 15 and 17 show the numbers of infected cells present in the supernatant through time for several different rotation rates. FIG. 15 shows that at a faster rotation rate of ½ rpm, more infected cells are left in the supernatant relative to the regular production (¼ rpm) and T-flask stationary controls. FIG. 16 confirms that the disappearance of infected cells from the supernatant correlates with the appearance of infectious foci on the cell monolayer. For all cases, the faster rpm resulted in fewer infectious foci per unit area.

FIG. 17 shows similar data for an experiment which tested ¼, and ⅛ rpm, where the slower rpm again resulted in enhanced transport of infected cells to the surface. The technique used for cell enumeration in FIG. 17 was much more sensitive than the technique used for cell enumeration in FIG. 15, so the ¼ rpm control cases for the two experiments differ.

EXAMPLE 6

Materials and Methods

The Oka strain of varicella was obtained from the Biken Institute, Japan. MRC-5 cells were obtained from ATCC or NIBSC and used to generate a Manufacturer's Working Cell Bank (MWCB) at Merck. MEM was manufactured by Merck and supplemented at the time of use with fetal bovine serum (FBS), neomycin and glutamine. HBME was purchased from GIBCO. Horseradish peroxidase-conjugated donkey anti-goat antibody (affinity purified F(ab')2 fragment) was obtained from Jackson Immunoresearch Labs, Inc., West Grove, Pa., (Cat# 705-036-147). The goat anti-varicella antiserum was obtained from Lampire, Inc. (Lot 2200). 3,3-diaminobenzidine (DAB) was obtained from Sigma, prepared as a 25 mg/ml solution in water and stored at −20° C. Immediately prior to use, DAB stock solution was thawed and diluted with a peroxide/nickel enhancing solution (Amersham) into phosphate buffer.

Establishment of a Cell Monolayer

Stationary Cell Expansion

MRC-5 ampules (ATCC No. CCL 171) were thawed, and the cells were cultivated in either T-flasks or Nunc Cell Factories, which are flat, stationary growth surfaces. The cells were added to BME medium supplemented with 10% FBS, 50 μg/mL neomycin, and 2 mM glutamine; and were incubated at 37° C. Every 3 to 9 days (depending upon the exact process), the cells were removed from the surface by enzymatic means using trypsin. The resulting cell suspension was then diluted and placed into a larger number of vessels for further propagation.

Roller Bottle Cell Expansion

Freshly trypsinized, concentrated cell suspension was placed in the roller bottles with MEM growth medium supplemented with 10% FBS, 50 μg/mL neomycin, and 2 mM glutamine. The bottles were incubated at 37° C. and rotated at the desired rate. After 4–6 days (depending upon the process used), the roller bottles were refed with fresh nutrient medium.

Cell Sedimentation Analysis

Roller Bottle Infection

Roller bottle cultures with an established cell monolayer on the roller bottle surface were infected by the addition of freshly trypsinized, virus-infected MRC-5 cells. The virus infected cells were added to the liquid nutrient medium in the roller bottle 6–8 days after the initial roller bottle cell plant.

Sonication of Harvested Fluids Samples

Samples were thawed in 20–30° C. water with frequent swirling. The sonicator was calibrated so that when the sonicator tip was immersed in 20 mL of room temperature water and energized for 1 minute, the temperature of the water would be increased by 5° C. The sonicator tip was then sterilized by the application of 90% isopropyl alcohol. The thawed samples were each sonicated for 1 minute in 20 mL aliquots. Sonicated samples were then frozen at −70° C. for potency testing.

Potency Testing

Frozen samples from the harvest were tested for the number of plaque forming units (PFU's) per mL using a standard plaque assay.

Varicella Plaque Assay

MRC-5 cells were grown in 60 mm plates with 5 ml/plate of BME with 10% FBS, 0.2% glutamine, and 0.05% neomycin. 10 plates were prepared per sample with 5 plates per dilution. The plates were then incubated at 35.5° C. with a 3% $CO_2$ gas environment for 2 days. Prior to addition of the samples, the cell growth medium was removed and 5 ml/plate of MEM with 2% FBS, 0.2% glutamine, and 0.05% neomycin was added to each plate. Diluted virus samples of 0.1 ml were added to each plate. Samples were diluted to ensure a plaque counting range of 15–80 plaques per plate. The plates were mixed well and incubated for 7 days at 35.5° C. with a 3% $CO_2$ gas environment. Following incubation, the medium was removed by aspiration and 2 ml of 0.2% Coomassie Blue stain in 100% ethanol containing 1% v/v glacial acetic acid were added to each plate. After 15 minutes at room temperature, the stain was removed and the plate was rinsed with cold water. The plates were inverted to dry. Plaques were then counted in each plate using a light box to assist in visualizing the plaques.

Particle Size Analysis

Particle counting and size analysis were performed using an Elzone Particle size analyzer model with a 48 μm orifice. Samples were diluted to 20 ml in PBS. The diluted sample was placed in the analyzer sample holder following calibration with particles of a known diameter (10 and 20 μm microspheres).

In situ Immunostaining Procedure

The medium was aspirated from the culture vessel (T-flask or roller bottle) using vacuum. The culture vessel was then rinsed three times with PBS with 1% BSA. After the final rinse with PBS, a fixing solution of 5% acetic acid, 5% water, and 90% methanol was added to the culture vessel and exposed to all surfaces for 15–30 minutes. The methanol was then aspirated from the culture vessel with vacuum. The culture vessels were then rinsed three more times with PBS, and stored with a PBS overlay at 4–8° C. until stained.

Immunostaining of the fixed bottles was carried out by a dual antibody method. First, 2–3 mls of a 1/500 dilution of goat anti-varicella antiserum in PBS with 1% BSA was added to the culture vessels, covering the entire growth surface of the T-flask and a 3–4 cm wide strip along one side of the roller bottle. The vessels were then placed on a rocker platform and rocked gently at room temperature for 1–2 hours to allow binding of the primary antibody. The culture vessels were then rinsed three times with PBS to remove unbound antibody, and 3 ml of a 1/500 dilution of the anti-goat antibody was added. The vessels were again incubated at room temperature with gentle rocking for 30–45 minutes. Unbound secondary antibody was then removed by three PBS rinses. Then, 10 ml of peroxidase substrate solution was added to each culture vessel and the vessels were incubated at 37° C. until foci of infected cells appeared. The peroxidase solution was then aspirated from the vessels with vacuum, and the vessels are again rinsed three times with PBS. The stained areas were left under a PBS overlay, and the vessels were stored at 4–8° C. Infecious foci were counted using a microscope at 10× magnification.

What is claimed is:

1. A method for enhancing the mixing of materials, wherein material is defined as a cell culture, virus infected cells or a virus, and media needed to sustain the cell culture, virus infected cells, and the virus, in a roller bottle which comprises the use of controlled axial flow perturbations, cross sectional flow perturbations, or both axial and cross-sectional flow perturbations in rotational roller bottle mixing.

2. The method for enhancing the mixing of materials in a roller bottle as recited in claim 1, wherein the controlled axial flow perturbations are introduced by a combination of a rocking motion in the vertical direction and constant rotation of the roller bottle along a horizontal axis.

3. The method for enhancing the mixing of materials in a roller bottle as recited in claim 2, wherein the rocking motion is generated by rocking the rollers that drive the roller bottle rotation.

4. The method for enhancing the mixing of materials in a roller bottle as recited in claim 3, wherein the rocking motion is defined by a rocking angle of about 0 degrees to about +10 degrees or −10 degrees, and a rock to roll frequency of about 0 to about 31.4.

5. The method for enhancing the mixing of materials in a roller bottle as recited in claim 2, wherein the rocking motion is generated by attaching a plurality of protuberances to the rollers that drive the roller bottle rotation.

6. The method for enhancing the mixing of materials in a roller bottle as recited in claim 2, wherein the rocking motion is generated by attaching a plurality of protuberances to the roller bottle.

7. The method for enhancing the mixing of materials in a roller bottle as recited in claim 1, wherein the controlled cross-sectional flow perturbations are introduced by using a time-dependent speed of rotation.

8. The method for enhancing the mixing of materials in a roller bottle as recited in claim 7, wherein the speed of rotation is varied about 0.01 to about 10 times the frequency of bottle rotation.

9. The method for enhancing the mixing of materials in a roller bottle as recited in claim 7, wherein the speed of rotation is varied either continuously or discontinuously, with a time dependent frequency.

10. The method for enhancing the mixing of materials in a roller bottle as recited in claim 1, wherein the controlled cross-sectional flow perturbations are introduced by reversing the direction of bottle rotation.

11. The method for enhancing the mixing of materials in a roller bottle as recited in claim 10, wherein the direction of rotation is varied about 0.01 to about 3 times the frequency of roller bottle rotation.

12. The method for enhancing the mixing of materials in a roller bottle as recited in claim 10, wherein the direction of rotation is varied either continuously or discontinuously, with a time dependent frequency.

13. The method for enhancing the mixing of materials in a roller bottle as recited in claim 1, wherein the controlled axial and cross-sectional flow perturbations are introduced by combining a rocking motion with time-dependent speed of rotation.

14. The method for enhancing the mixing of materials in a roller bottle as recited in claim 13, wherein the rocking motion is generated by rocking the rollers that drive roller bottle rotation.

15. The method for enhancing the mixing of materials in a roller bottle as recited in claim 13, wherein the rocking motion is generated by attaching a protuberance to the rollers that drive the roller bottle rotation.

16. The method for enhancing the mixing of materials in a roller bottle as recited in claim 13, wherein the rocking motion is generated by attaching a protuberance to the roller bottle.

17. The method for enhancing the mixing of materials in a roller bottle as recited in claim 13, wherein the rocking motion is defined by a rocking angle of about 0 degrees to about +10 degrees or −10 degrees, and a rock to roll frequency of about 0 to about 31.4 and a time-dependent rotation speed varied a frequency of about 0.01 to about 10 times the roller bottle rotation speed.

18. The method for enhancing the mixing of materials in a roller bottle as recited in claim 17, wherein the rocking speed and the speed of rotation are varied, either continuously or discontinuously, with a time-dependent frequency.

19. The method for enhancing the mixing of materials in a roller bottle as recited in claim 1, wherein the controlled axial and cross-sectional flow perturbations are introduced by combining rocking motion and time-dependent direction of rotation.

20. The method for enhancing the mixing of materials in a roller bottle as recited in claim 19, wherein the rocking motion is generated by rocking the rollers that drive roller bottle rotation.

21. The method for enhancing the mixing of materials in a roller bottle as recited in claim 19, wherein the rocking motion is generated by attaching a protuberance to the rollers that drive the roller bottle rotation.

22. The method for enhancing the mixing of materials in a roller bottle as recited in claim 19, wherein the rocking motion is generated by attaching a protuberance to the roller bottle.

23. The method for enhancing the mixing of materials in a roller bottle as recited in claim 19, wherein the rocking motion is defined by a rocking angle of about 0 degrees to about +10 degrees or about −10 degrees, and a rock to roll frequency of about 0 to about 31.4, and a time-dependent direction which is varied about 0.01 to about 3 times the frequency of roller bottle rotation.

24. The method for enhancing the mixing of materials in a roller bottle as recited in claim 23, wherein the rocking speed and the direction of rotation are varied, either continuously or discontinuously, with a time-dependent frequency.

25. The method for enhancing the mixing of materials in a roller bottle as recited in claim 1, wherein the controlled axial and cross sectional flow perturbations are introduced by combining a rocking motion, a time dependent speed of rotation, and a time-dependent direction of rotation.

26. The method for enhancing the mixing of materials in a roller bottle as recited in claim 25, wherein the rocking motion is generated by rocking the rollers that drive roller bottle rotation.

27. The method for enhancing the mixing of materials in a roller bottle as recited in claim 25, wherein the rocking motion is generated by attaching a protuberance to the rollers that drive roller bottle rotation.

28. The method for enhancing the mixing of materials in a roller bottle as recited in claim 25, wherein the rocking motion is generated by attaching a protuberance to the roller bottle.

29. The method for enhancing the mixing of materials in a roller bottle as recited in claim 25, wherein the rocking motion is defined by a rocking angle of about 0 degrees to about +10 or about −10 degrees and a rock to roll frequency of about 0 to about 31.4, and the time dependent direction of rotation is varied about 0.01 to about 3 times the frequency of roller bottle rotation and the speed of rotation is varied a frequency of about 0.01 to about 10 times the frequency of roller bottle rotation.

\* \* \* \* \*